(12) United States Patent
Sullivan et al.

(10) Patent No.: US 8,252,527 B2
(45) Date of Patent: Aug. 28, 2012

(54) METHOD FOR IDENTIFICATION OF POLYNUCLEOTIDES CAPABLE OF CLEAVING TARGET MRNA SEQUENCES

(75) Inventors: John M. Sullivan, Hamburg, NY (US); Edwin H. Yau, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 405 days.

(21) Appl. No.: 12/070,561

(22) Filed: Feb. 19, 2008

(65) Prior Publication Data

US 2008/0227103 A1  Sep. 18, 2008

Related U.S. Application Data

(60) Provisional application No. 60/890,276, filed on Feb. 16, 2007.

(51) Int. Cl.
   *C12Q 1/68* (2006.01)
(52) U.S. Cl. ........... 435/6; 435/325; 435/375; 536/24.5; 536/24.31; 536/24.1
(58) Field of Classification Search .................. None
   See application file for complete search history.

(56) References Cited

U.S. PATENT DOCUMENTS

| | | | |
|---|---|---|---|
| 4,937,190 A | 6/1990 | Palmenberg et al. | |
| 5,695,992 A | 12/1997 | Lieber et al. | |
| 6,255,071 B1* | 7/2001 | Beach et al. | 435/69.1 |
| 2002/0082225 A1* | 6/2002 | Blatt et al. | 514/44 |
| 2005/0112095 A1* | 5/2005 | Hsu et al. | 424/93.2 |
| 2006/0121466 A1 | 6/2006 | Khvorova et al. | |

OTHER PUBLICATIONS

Citti et al. Synthetic hammerhead ribozymes as therapeutic tools to control disease genes. Current Gene Therapy 2005, vol. 5:11-24.*

Cullen, Bryan. Utility of the Secreted Placental Alkaline Phosphatase Reporter Enzyme. Methods in Enzymology, vol. 326, 2000: 159-160.*

Lee, et al.; High-Efficiency Protein Expression Mediated by Enterovirus 71 Internal Ribosome Entry Site; Biotechnology and Bioengineering, vol. 90, No. 5, Jun. 5, 2005; pp. 656-662.

Khvorova, et al.; Sequence elements outside the hammerhead ribozyme catalytic core enable intracellular activity; Nature Structural Biology, vol. 10, No. 9, Sep. 2003; pp. 708-712.

Krüger, et al.; Involvement of Proteasome α-Subunit PSMA7 in Hepatitis C Virus Internal Ribosome Entry Site-Mediated Translation; Molecular and Cellular Biology, vol. 21, No. 24, Dec. 2001; pp. 8357-8364.

Sullivan, et al.; Hammerhead ribozymes designed to cleave all human rod opsin mRNAs which cause autosomal dominant retinitis pigmentosa; Molecular Vision 2002, vol. 8; pp. 102-113.

Zur Förderung Der Wissenschaften, et al.; Selection of Efficient Cleavage Sites in Target RNAs by Using a Ribozyme Expression Library; Molecular and Cellular Biology, vol. 15, No. 1, Jan. 1995; pp. 540-551.

Zakharchuk, et al.; The fowl adenovirus type 1 (CELO) virus-associated RNA-encoding gene: a new ribozyme-expression vector; Elsevier Science, 1995; pp. 189-193.

* cited by examiner

*Primary Examiner* — Kimberly Chong
(74) *Attorney, Agent, or Firm* — Hodgson Russ LLP

(57) ABSTRACT

Provided are methods for identifying a polynucleotide that can reduce the level of a target mRNA. The method can be performed by providing cells that express an RNA polynucleotide that contains a target mRNA sequence, an internal ribosome entry sequence (IRES) and a sequence encoding a secreted reporter protein; introducing to the cells a test polynucleotide, and measuring activity of the secreted reporter protein. A reduction in secreted reporter protein activity relative to a control cell into which the test polynucleotide has not been introduced is indicative that the test polynucleotide is capable of reducing the level of the target mRNA in the cells. The method is adaptable for high throughput screening methods and is suited for identifying polynucleotides that can catalyze cleavage of target mRNA and/or act on target mRNA through and antisense or RNAi mechanism.

12 Claims, 8 Drawing Sheets

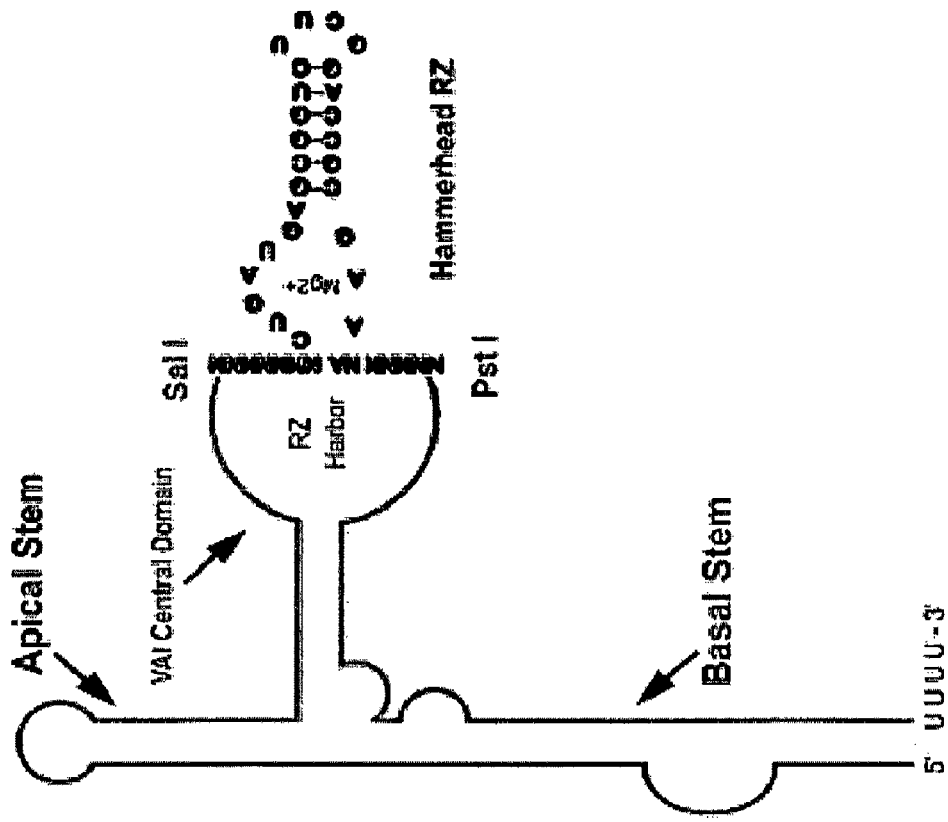
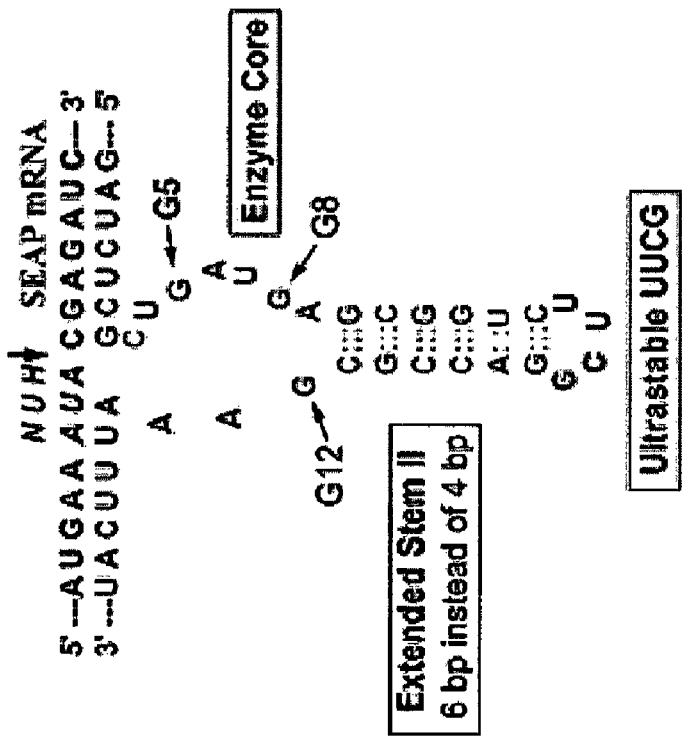

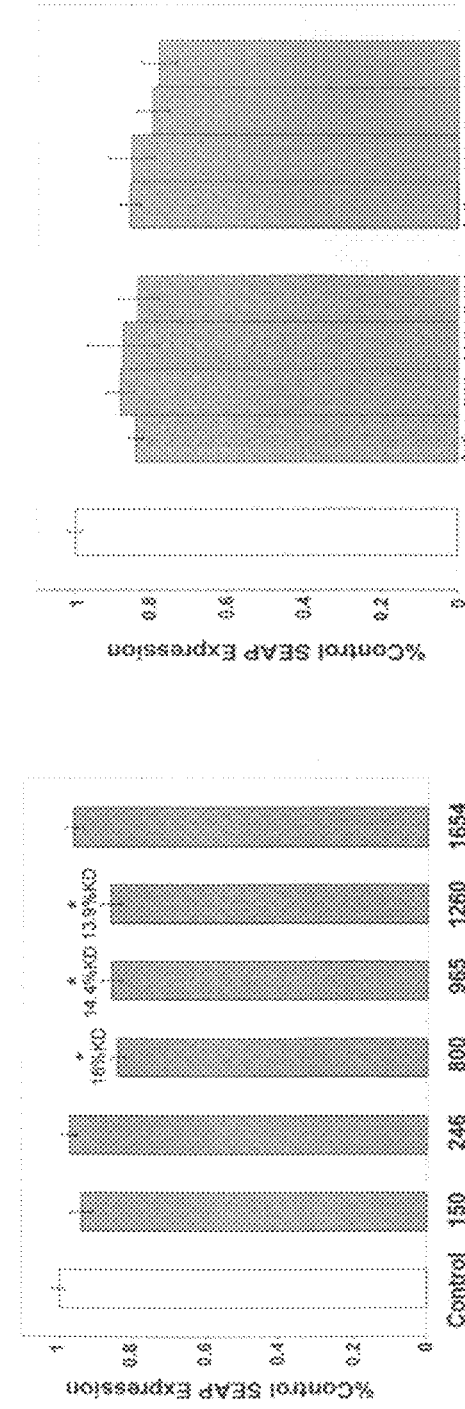
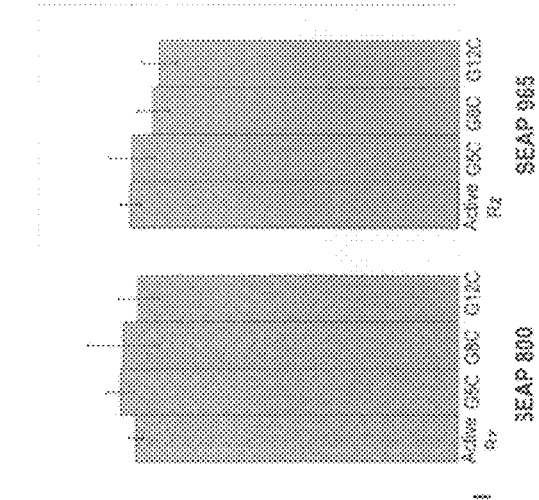
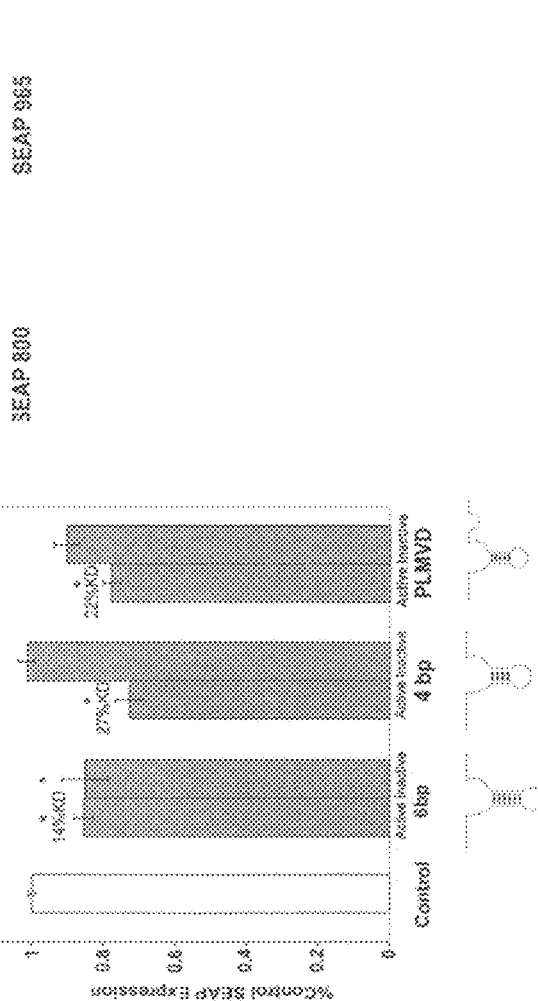
Figure 3A
Figure 3B
Figure 3C

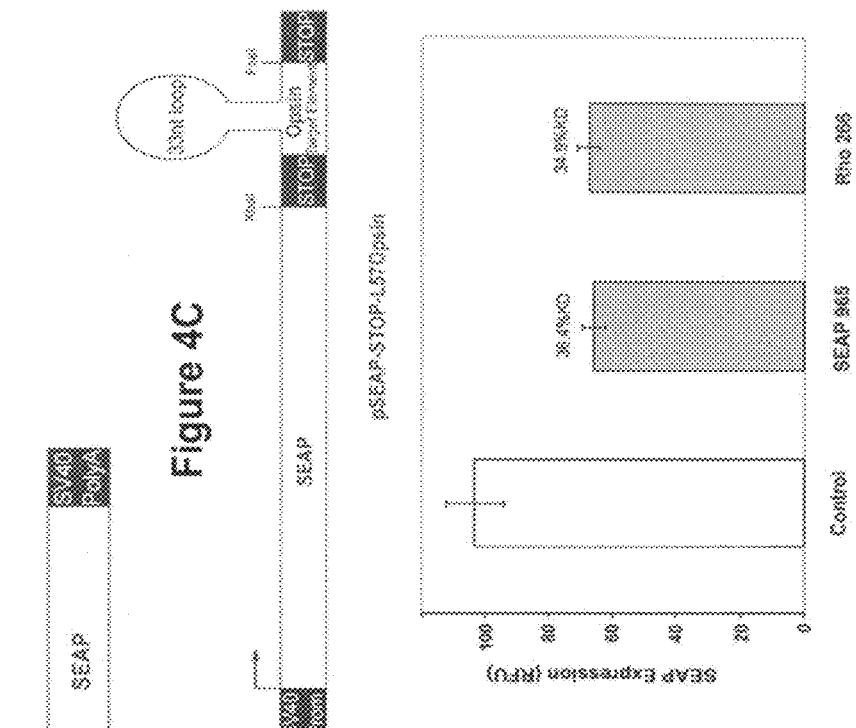
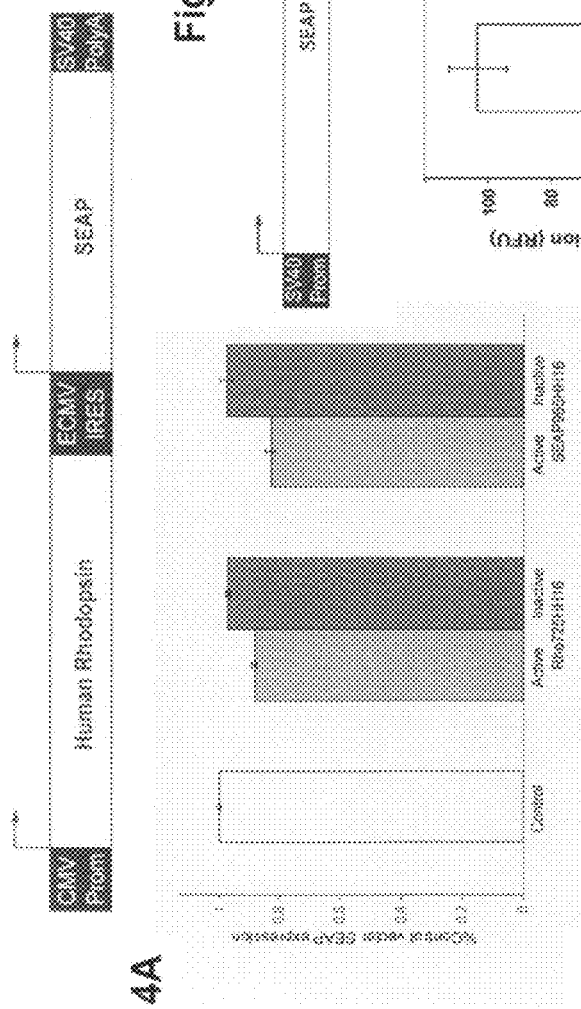
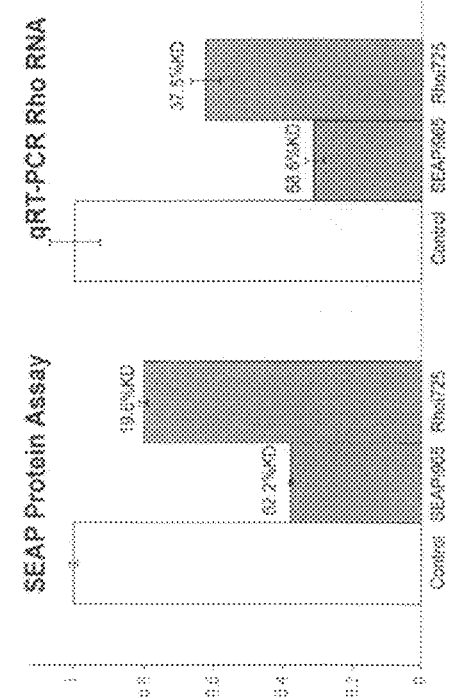
Figure 4A
Figure 4B
Figure 4C

METHOD FOR IDENTIFICATION OF POLYNUCLEOTIDES CAPABLE OF CLEAVING TARGET MRNA SEQUENCES

This application claims priority to application Ser. No. 60/890,276, filed on Feb. 16, 2007, the entire disclosure of which is incorporated herein by reference.

This work was supported by Grant No. R01 EY13433 from the National Eye Institute. The Government has certain rights in the invention.

FIELD OF THE INVENTION

The present invention relates generally to identification of agents that can modulate post transcriptional gene expression and more particularly to identification of polynucleotides that can reduce levels of target mRNA in vivo.

BACKGROUND OF THE INVENTION

The challenge of successful design of a nucleic acid-based agent, be it ribozyme, antisense, or siRNA, for reducing the level of a disease related or other target mRNA, engages biocomplexity at many levels. One of the profound difficulties in discovering such agents for use in post-transcriptional gene silencing (PTGS) approaches is that classical molecular biology techniques, such as Western and Northern blotting, are very slow and are generally not quantitative. Further, target mRNA is folded into dense secondary and tertiary structure, may be coated with heterogeneous proteins, undergoes dynamic fluctuations in structure and resides in cells with characteristic lifetimes in intracellular compartments (nucleus, cytoplasm, ribosomes, etc.), all of which constrain the range of timescales and spatial environments available for PTGS interaction with the target mRNA. Within this milieu, target mRNA must present stable regions of accessibility for PTGS ligand interaction. Moreover, the PTGS agent must be present in the same spatial locale as the target mRNA, at sufficient concentrations to allow effective diffusion limited interaction, and in conformational state(s) that enable effective processing of target mRNA, on its proscribed time scales, for successful reduction of the target mRNA to be realized. The nature of these challenges, at both the target mRNA and PTGS agent levels, is a major factor for the slow entry of PTGS agents into the pharmaceutical market, despite their obvious potential. Thus, there is an ongoing need for methods for identifying agents that can be used to reduce the levels of a target mRNA.

SUMMARY OF THE INVENTION

The present invention provides a method for identifying a test polynucleotide that is capable of reducing the level of a target mRNA in a cell. The method comprises the steps of providing cells that express an RNA polynucleotide, wherein the RNA polynucleotide comprises a target mRNA sequence, an internal ribosome entry sequence (IRES) and a sequence encoding a secreted reporter protein, and introducing a test polynucleotide to the cells. Detecting a reduction in activity of the secreted reporter protein relative to control cells into which the test polynucleotide was not introduced is indicative that the test polynucleotide is capable of reducing the target mRNA in the cell.

It is expected that the method of the invention can be used to identify polynucleotides that can reduce the level of any target mRNA. In connection with this, the target mRNA may encode a complete or a partial open reading frame, so long as the target mRNA sequence adopts a structure comprising a single stranded sequence that is also present in the mRNA encoding the complete open reading frame. The target mRNA may also comprise untranslated regions of mRNA transcripts.

The test polynucleotide may be any polynucleotide. In particular embodiments, the test polynucleotide is a ribozyme, such as a hammerhead ribozyme ("hhRz"), an antisense RNA, an siRNA, a DNAzyme, a hairpin ribozyme, or a Hepatitis Delta Virus ribozyme. The nucleotide sequence of the test polynucleotides can be designed based upon computational or experimental analysis of the target mRNA sequence employed to yield predictions as to single stranded regions which comprises sequences that are expected to have complementarity to the test polynucleotides. In one embodiment, analysis of the target mRNA sequence can be performed using one or a combination of computer programs, such as programs available to the public, which include but are not limited to MFold (available at frontend.bioinfo.rpi.edu/applications/mfold), SFold (available at sfold.wadsworth.org/), and OligoWalk (available at rna.urmc.rochester.edu/cgibin/server_exe/oligowalk/oligowalk_form.cgi). In an alternative embodiment, experimental techniques can be used to for analysis of the target mRNA sequence, such as oligonucleotide mediated RNaseH mapping.

The IRES used in the RNA comprising the target mRNA sequence may be any IRES sequence. In a preferred embodiment, the IRES is a wild-type or modified Encephalomyocarditis virus IRES or Hepatitis C Virus IRES.

The secreted reporter protein may be any secreted reporter protein. In a preferred embodiment, the secreted reporter protein encoded in the RNA molecule that comprises the target mRNA sequence is secreted placental alkaline phosphatase (SEAP) (Berger J et al. (1988) *Gene* 66: 1-10).

The test polynucleotide of the invention, as well as the RNA polynucleotide comprising the target mRNA sequence, the IRES, and the sequence encoding a secreted reporter protein, may be introduced to the cells using any suitable methods, such as by transient or stable transfection of DNA templates encoding ribopolynucleotide sequences that are transcribed by the cells. Alternatively, the test polynucleotides may be prepared in advance and introduced to the cells as intact unmodified or modified DNA or RNA molecules with base modifications to increase stability. The test polynucleotides may be provided in single or double stranded form.

The method of the invention is adaptable for high throughput screening (HTS) approaches, such as by testing in multiwell formats. This can be achieved by distributing cells expressing an RNA comprising the target mRNA sequence, the IRES and the sequence encoding a secreted reporter protein into a plurality of reactions and introducing into the cells in each reaction a distinct test polynucleotide. Detecting a reduction in reporter activity in a particular reaction is indicative that the test polynucleotide introduced into the reaction is capable of reducing the level of target mRNA in the cells. It is expected that such methods can be partially or completely roboticized so as the enhance the efficiency of the screen.

BRIEF DESCRIPTION OF THE FIGURES

FIG. 2a provides a graphical representation of computational predictions of hhRz secondary structure (SEQ ID NO:36).

FIG. 2b provides a graphical representation of adenoviral (VAI)-hhRz-Chimera constructs which contain a Hammerhead RZ sequence (SEQ ID NO:37).

FIG. 3a provides a graphical representation of results obtained by testing catalytic efficacy with various hhRz-VA1 constructs in 96-well format for reductions in SEAP activity.

FIG. 3b provides a graphical representation of results obtained from functional analysis of SEAP protein knockdown by hhRz in human cells and shows that there is evidence of antisense or enzymatic catalysis in stabilized 6 base pair hhRz designs.

FIG. 3c provides graphical representation of results obtained from functional analysis of SEAP protein knockdown by optimizations of a 6 base pair stabilized hhRz construct tested against the accessible SEAP 965 site or a 4 bp classical hhRz tested against accessible SEAP 965, or a Peach Latent Mosaic Virus construct tested against the accessible SEAP 965 site.

FIG. 4a provides a graphical representation of an embodiment of a dicistronic RNA utilized in the method of the invention that comprises an RNA transcript encoding both Rho and SEAP proteins.

FIG. 4b provides a graphical representation of SEAP analysis obtained using pSUPER shRNA designed to target the SEAP 965 region (SEAPi965) and the Rho 725 region (Rhoi725).

FIG. 4c) provides a graphical representation of a predicted loop (33 nucleotides) capping a stable stem structure in the region around nucleotide (nt) 250 in human rod opsin mRNA identified and results obtained from analyses of the same.

DETAILED DESCRIPTION OF THE INVENTION

Figure 1:
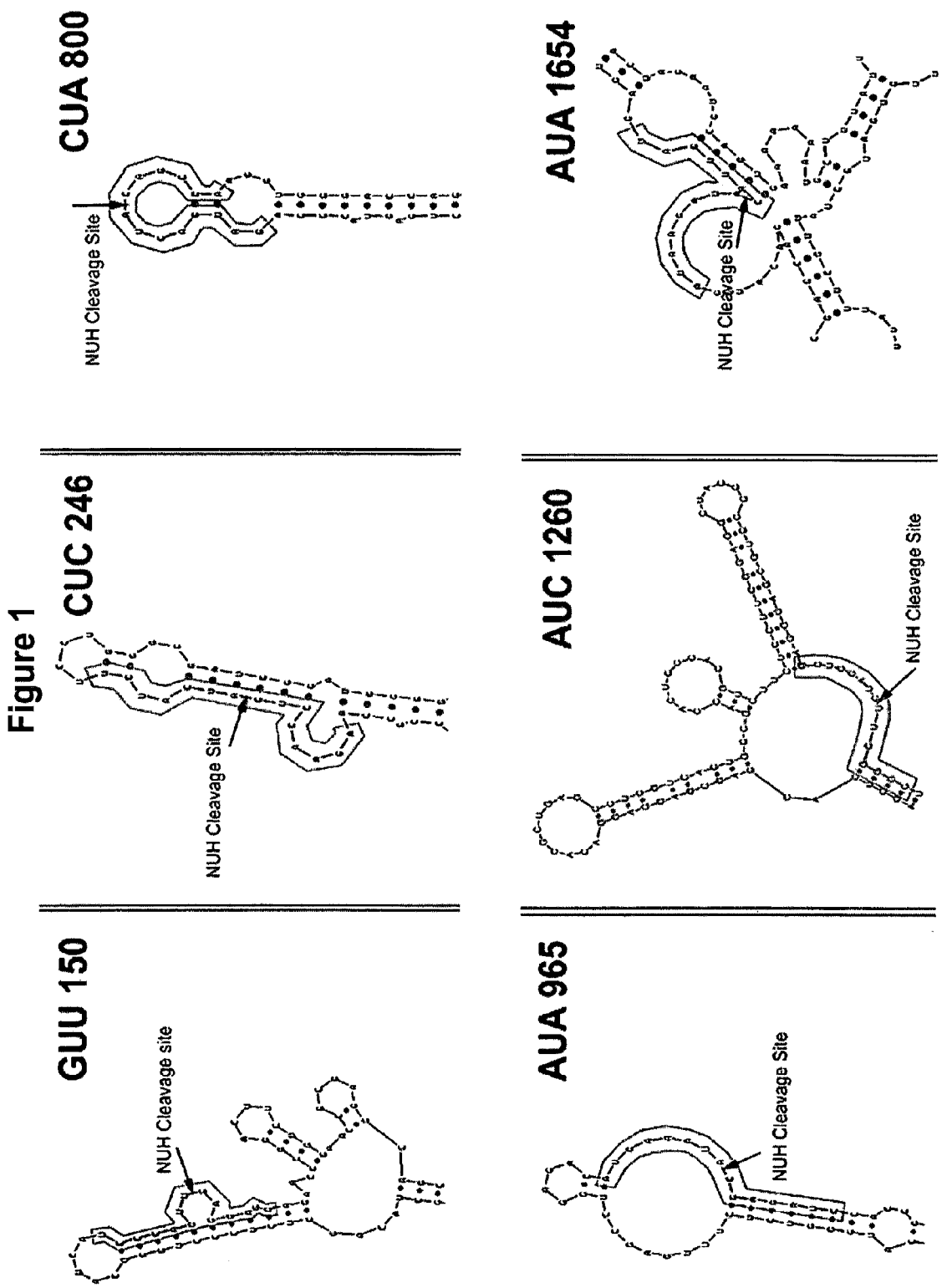
FIG. 1 provides a graphical representation of computational predictions of SEAP mRNA secondary structure and shows the most stable structure of the local region (200 base pairs) around each selected target as determined by an energy minimization algorithm (MFold) over a 20% sub-optimal range. Target regions are shaded, and NUH↓ (hammerhead site, N=any nucleotide, U=U, H=C, A or U, but not G, down arrow indicates location of phosphodiester bond that is cleaved) target sites are labeled with arrows. Riobzyme sequences shown are: GUU150: (SEQ ID NO:30); CUC246: (SEQ ID NO:31); CUA800: (SEQ ID NO:32); AUA965: (SEQ ID NO:33); AUC1260: (SEQ ID NO:34); AUA1654: (SEQ ID NO:35).

The present invention provides a method for identifying a test polynucleotide that is capable of reducing the level of a target mRNA in a cell.

The method comprises providing cells expressing an RNA comprising a target mRNA sequence, an internal ribosome entry sequence (IRES) and a sequence encoding a secreted reporter protein, and introducing a test polynucleotide to the cells. A reduction in reporter activity relative to control cells into which the test polynucleotide is not introduced is indicative that the test polynucleotide is capable of reducing the amount of target mRNA in the cell. It will be recognized that other controls may also be used, such as polynucleotides that have been modified so as not to act on the target site, or polynucleotides with known activity against a sequence in the target mRNA.

The RNA comprising the target mRNA sequence, the IRES and the sequence encoding a secreted reporter protein is also referred to herein as a "bicistronic RNA." However, it should be recognized that such an RNA is not necessarily limited to comprising only two cistrons (i.e., only two open reading frames).

The method of the invention is amenable to high throughput screening approaches by distributing cells expressing an RNA comprising a target mRNA sequence, an IRES and a sequence encoding a secreted reporter protein into a plurality of reactions and introducing to the cells in each reaction a distinct test polynucleotide. Detecting a reduction in reporter activity in a particular reaction relative to a control into which a test polynucleotide has not been introduced is indicative that the test polynucleotide introduced into the reaction is capable of reducing the level of target mRNA in the cells. The reactions into which the cells are distributed can be any suitable apparatus for holding cells, including but not limited to wells in microtitre plates, tubes, such as test tubes or Eppendorf tubes, and the like, or HTS plates with multiple test wells.

It is expected that the strategy provided by the invention can be used to identify polynucleotides that can reduce the level of any target mRNA, such as those involved in disease processes. In this regard, the target mRNA may comprise a complete open reading frame encoding a complete protein, or it may comprise a partial open reading frame encoding a portion of a protein, so long as the mRNA comprises enough target mRNA sequence to facilitate formation of structures that are expected to provide at least one single stranded region against which test polynucleotides can be analyzed according to the method of the invention. The target mRNA may also comprise untranslated regions of mRNA transcripts, which may also comprise accessible regions against which the test polynucleotides may be tested.

The bicistronic mRNA and/or the test polynucleotides used in the present invention may be expressed as polynucleotides in cells from any of a variety of DNA templates introduced into the cells using any conventional method. The test polynucleotides may also be introduced to cells as unmodified or synthetic nucleotides, such as polyribonucleotides with ribose base modifications to increase stability. The test polyribonucleotides may be single stranded, or double stranded.

It is considered that polynucleotides identified according to the method of the invention are candidates for use in post-transcriptional gene silencing ("PTGS") modalities.

In varying embodiments, the test polynucleotide may be a ribozyme, such as a hammerhead ribozyme ("hhRz"), an antisense RNA, an siRNA, a DNAzyme, a hairpin ribozyme, or a Hepatitis Delta Virus ribozyme.

The test polynucleotides used in the invention can be designed to specifically pair with virtually any predicted single stranded RNA sequence, and thus are each considered to have an antisense (AS) component. In this regard, the interaction between a test polynucleotide identified by the method of the invention and the bicistronic RNA depends upon annealing between target RNA and the AS component of the test polynucleotides. Thus, when the test polynucleotide is a ribozyme, such as a hammerhead ribozyme that can cleave the target mRNA, it binds to an accessible region of target mRNA, cleaves the target RNA, and then dissociates from the target and performs the same series of reactions (enzymatic turnover) with other substrate mRNA molecules. Ribozymes generally bind to target RNA with sufficient strength to insure a hybrid lifetime that allows chemical cleavage of target RNA, but not so strongly that the product dissociation is slow and inhibits turnover (product inhibition). Hammerhead ribozymes are know to cleave at a consensus sequence triplet with a central U which can be described as NUH ↓, where N can be any nucleotide and H any nucleotide but G, and where the arrow identifies the cleavage site.

When the test polynucleotide of the invention is an antisense mRNA that can anneal to a target mRNA sequence, it is believed that it induces RNaseH mediated cleavage of double stranded target mRNA/test polynucleotide, and/or inhibits translation by mechanical impedance of ribosome progression along the mRNA, which in turn results in reduced levels of reporter protein activity.

The test polynucleotide of the invention may be also be an RNA interfering (RNAi) agent, such as an siRNA. RNAi agents are commonly expressed in cells as short hairpin RNAs (shRNA), or introduced to cells as chemically stabilized short interfering RNAs (siRNAs). As is recognized in the art, expressed shRNAs are believed to be cleaved in the nucleus by Drosha endonuclease and further processed by the cytoplasmic nuclease Dicer III, to achieve a mature RNAi. The double stranded RNAi is recognized by the RNA-induced silencing complex (RISC), which selects the AS strand on the basis of designed thermodynamic end stability, and then uses this charged RISC to anneal to accessible regions of target RNAs to promote target cleavage. The RISC complex is tolerant of several mutations in the typical 14 nt long AS stretch that allows target recognition. In addition, siRNAs can simulate microRNAs and bind to the 3' untranslated region of mRNAs to inhibit translation.

The test polynucleotide may also be a DNAzyme, which are deoxyribonucleotides that can exhibit catalytic activity against a target sequence.

Predicting an accessible region of a target mRNA is considered a significant difficulty in PTGS development because highly accessible sites are rare in any mRNA. Further, all PTGS technologies are conditionally dependent upon a rate-limiting second-order molecular annealing event in vivo. Moreover, there are limitations to computational algorithms (i.e., only some secondary structures are predicted, and then only to a given level of confidence, while tertiary structures, protein coating, and dynamic fluctuations are not predicted), which necessitates cumbersome validation of targets when using previously available methods for such validation. Nevertheless, computer-based algorithms can be employed to predict stable secondary structural motifs that harbor large single stranded (ss) platforms that are accessible for second order annealing reaction with a small RNA ligand. Thus, there are available experimental and computational approaches to predicting accessible sites in RNAs for use in designing the test polynucleotides used in the method of the present invention. In this regard, specific computer programs and combinations thereof may be employed for prediction of accessible regions in the target mRNA. Suitable computer programs for this purpose are available to the public and include but are not limited to MFold (available at frontend.bioinfo.rpi.edu/applications/mfold), SFold (available at sfold.wadsworth.org/), and OligoWalk (available at rna.urmc.rochester.edu/cgibin/server_exe/oligowalk/oligo-walk_form.cgi). In another embodiment, analysis of the target mRNA sequence can be performed experimentally, such as by oligonucleotide mediated RNaseH mapping.

The target mRNA may be analyzed using a single or a combination of computer programs to estimate both steric and energetic features of local RNA folding. For example, MFold may be used to obtain a rigorous statistical analysis of the probabilities of sterically accessible regions in predicted mRNA folding patterns. MFold data may be further analyzed with SFold. SFold employs an independent algorithm that is not dependent upon free energy ($\Delta G$) minimization to determine access probabilities. Further, OligoWalk may be utilized to analyze local free energy (LFE) along the target RNA. All the parameters obtained by such computer analysis may then be convolved and ranked to determine the most likely accessible regions. mRNA Accessible Site Tagging (MAST) is another high throughput (HTS) approach available to screen target mRNA sequences for accessibility.

Determining whether a test polynucleotide is capable of reducing the level of a target mRNA in a cell can be performed by detecting a reduction in activity of a secreted reporter protein relative to activity of the reporter in a cell into which the test polynucleotide has not been introduced. In this regard, it is expected that any fluorescent protein, or chloramphenicol acetyl transferase, beta-galactosidase, or LacZ, could be engineered with secretory elements to promote sufficient secretion of translated reporter protein into the extracellular milieu for use in the method of the invention. Suitable examples of reporter proteins include but are not limited to a secreted form of EGFP (Katagiri Y and Ingham K C (2002) BioTechniques 33: 24-26), a secreted form of luciferase (Markova et al. (2004) J. Biol. Chem. 279: 3212-3217) and a luciferase-GFP fusion protein (Liu J, et al., (2000) Luminescence 15: 45-49).

In a preferred embodiment, the secreted reporter protein that is contained in the bicistronic mRNA is a secreted placental alkaline phosphatase (SEAP) (Berger J et al. (1988) *Gene* 66: 1-10). The SEAP enzyme is a truncated form of human placental alkaline phosphatase. Removal of the transmembrane domain of the protein allows it to be secreted from the cells into the surrounding media. SEAP activity can be detected by a variety of methods including, but not limited to, measurement of catalysis of a fluorescent substrate (luminescence), immunoprecipitation, HPLC, and radiometric detection. The luminescent method is preferred due to its increased sensitivity over calorimetric and immunodetection methods. Further, approximately 95% of the SEAP protein is secreted from the cells, the level of extracellular SEAP protein is directly proportional to the steady-state levels of mRNA containing SEAP cDNA, and SEAP can be employed in a highly efficient chemifluorescence assay which also allows kinetic measures of reduction in target mRNA in live cells over time, since it is possible to conduct the assay on only the extracellular fluid, and thus, the cells need not be lysed to perform the assay. Examples illustrating the use of SEAP in the method of the invention are detailed below.

The IRES used in the RNA comprising the target mRNA sequence may be any IRES sequence. A variety of suitable IRES sequences are known in the art and may be used, so long as they are capable of recruiting translation initiation factors to the downstream open reading frame(s) of the mRNA. IRES sequences are normally identical to or are derived from viral sequences. However, other suitable IRES sequences may be obtained from other organisms, including but not limited to mammal, insect, and yeast. In a preferred embodiment, the IRES is a wild-type or modified Encephalomyocarditis virus IRES or a Hepatitis C Virus IRES.

In one embodiment, the IRES sequence can be located 3' to target mRNA sequence and 5' to the open reading frame of the reporter protein coding sequence. Such positioning permits the ribosome to bind 5' to the open reading frame and initiate translation of the reporter protein open reading frame.

In one embodiment, we employ SEAP as both a hhRz target and an HTS reporter molecule and demonstrate a statistically significant knockdown of SEAP production by two lead candidate hhRzs expressed as chimeric RNAs within a modified adenoviral VA1 RNA structure. Potentially accessible sites in the SEAP mRNA were computationally predicted using algorithms based upon different thermodynamic principles. Three out of four predicted sites were significantly suppressed, establishing the viability of computational approaches for identifying accessible target sites in the method of the invention. However, near the 3' end of the target mRNA a site (position 1654) was predicted to be accessible but proved insensitive to knockdown. This result emphasizes that experimental validation of in silico predicted accessibility according to the method of the invention is still required.

Our experiments showed that the extension of hhRz stem II to 6 bp to stabilize hhRz folding abolishes catalytic activity. Extension of stem-II by two base pairs certainly stabilizes folding to a discrete structural state, but somehow inhibits an aspect of catalysis (e.g. decreased catalytic rate, increased religation rate). The HTS system showed this deficiency and allowed us to modify and rapidly revise the hhRz into clearly enzymatic forms. Restoration of the natural 4 bp stem II length restored the catalytic ability in the cellular environment. The addition of tertiary elements significantly improved the level of knockdown compared to the extended 6 base pair hhRz construct, but did not perform any better compared to the classical 4 base pair construct. This stands in contrast to experiments with cis-acting ribozymes, where adjacent tertiary elements exert profound effect on catalytic activity (De la Pena, et al. (2003) EMBO J. 22, 5561-70; Khvorova, et al. (2003) Nat. Struct. Biol. 9, 708-712; Penedo, et al. (2004) RNA 10, 880-888), which illustrates the need for the method of the present invention to analyze a plurality of test polynucleotides for trans-acting catalytic activity in living cells. In connection with this, it is expected that hhRz core, Stem-II, and accessory elements identified according to the method of the invention could be directly adapted to any other target mRNA simply by appending appropriate targeting antisense flank sequences.

In another embodiment, we integrated the SEAP cDNA into constructs that express all or part of a model disease target mRNA (Rho). Expression of the target RNA is directly linked to SEAP protein expression. This allows HTS testing of hhRz or other polynucleotide-based agents against the model target RNA. Two formats were explored, a bicistronic mRNA containing Target-IRES-SEAP and a SEAP mRNA in which structured elements of the target mRNA are embedded in the 3'UT region. These technologies are also expected to be extendable to any target mRNA sequence. This approach has reduced the time scale of PTGS development and optimization by at least two orders of magnitude compared to classical approaches used previously that involved slow, variable, and cumbersome tools (e.g. Western analysis). Incorporation of robotic tools onto this platform is expected to greatly extend current capacity by enhancing speed in sample processing and further minimizing variation due to manual pipetting.

The following Examples are intended to illustrate but not limit the present invention.

Example 1

This Example provides a description of materials and methods and that were employed in the development of the present invention, as well as the results of analysis of test polynucleotides as candidates for reducing the level of target mRNA in cells.

Computational models of RNA Secondary Structure Prediction. The secondary structure of full length SEAP mRNA from pSEAP2-control plasmid (Clontech) was subjected to analysis, using both free energy minimization (MFold algorithm) (Zuker, M. (2003) Nucleic Acids Res. 31, 3406-3415) and a Boltzmann-weighted sampling of all sub-structures (SFold algorithm) (Ding, et al. (2004) Nucleic Acids Res. 32, W135-W141). Using MFold, SEAP target mRNA was folded in 200 nucleotide windows with 100 nucleotide overlapping steps, and a range of structures within 20% of the minimal free energy structure with a maximum of 20 structures were generated for each window. The total ensemble of structures was analyzed for large single-stranded bulges or loops (greater than or equal to 7 nt) that contained potential hhRz target sites (NUH ↓). The probabilities of the large single-stranded structures generated by MFold was calculated and averaged with the probability of the site being single-stranded as directly predicted with SFold.

Vectors and Cloning. Ribozyme cDNA constructs were directionally ligated into the Sal I/Pst I sites in a VA1 expression vector (pUC-VAL). The pUC-VAL vector was designed as a much enhanced next-generation sibling of the already successful pG-VAL vector (Lieber, A. and Strauss, M. (1995) Mol. Cell. Biol. 15, 540-51). Ribozyme cDNA sequences (bases changed for catalytic inactive mutations are in bold and are italicized): SEAP150 (FOR: (SEQ ID NO:2: 5'-TCGACCCTCCTCCTGATGAGCGGTCTTCG-GACCGCGAAACTGGGTCTGCA-3' REV: SEQ ID NO:3: 3'-GGGAGGAGGACTACTCGCCAGAAGCCTG-GCGCTTTGACCCAG-5'); SEAP 246 (SEQ ID NO:4) (FOR: 5'-TCGACAGATGATCTGATGAGCGGTCT-TCGGACCGCGAAAGGTTCTCTGCA-3', REV: (SEQ ID NO:5) 3'-GTCTACTAGACTACTCGCCAGAAGCCTG-GCGCTTTCCAAGAG-5'); SEAP 800 (SEQ ID NO:6) (FOR: 5'-TCGACTTGGCTGCTGATGAGCGGTCT-TCGGACCGCGAAAGTCATCCTGCA-3', (SEQ ID NO:7) REV: 3'-GAACCGACGACTACTCGCCAGAAGCCTG-GCGCTTTCAGTAGG-5'); SEAP 965 (FOR: (SEQ ID NO:8) 5'-TCGACGATCTCGCTGATGAGCGGTCT-TCGGACCGCGAAATTTCATCTGCA-3', REV: (SEQ ID NO:9) 3'-GCTAGAGCGACTACTCGCCAGAAGCCTG-GCGCTTTAAAGTAG-5'); SEAP 1260 (SEQ ID NO:10) (FOR: 5'-TCGACGCCCGAACTGATGAGCGGTCT-TCGGACCGCGAAATGGAGCCTGCA-3', (SEQ ID NO:11) REV: 3'-GCGGGCTTGACTACTCGCCAGAAGC-CTGGCGCTTTACCTCGG-5'); SEAP 1654 (SEQ ID NO:12) (FOR: 5'-TCGACATCAATGCTGATGAGCG- GTCTTCGGACCGCGAAATCTTATCTGCA-3', (SEQ ID NO:13) REV: 3'-GTAGTTACGACTACTCGCCAGAAGC-CTGGCGCTTTAGAATAG-5'); SEAP 965 PLMVd (SEQ ID NO:14) (FOR: 5'-TCGACGTGGATAATCTCGCTGAT-GAGTCGCTGGGATGCGACGAAATTT CATCTGCA-3', (SEQ ID NO:156) REV: 3'-GCACCTATTAGAGCGAC-TACTCAGCGACCCTACGCTGCTTTAAAGTAG-5');
SEAP 965 4 bp (SEQ ID NO:16) (FOR: 5'-TCGAC-GATCTCGCTGATGAGGCCGAAAGGCCGAAA TTTCATCTGCA-3', (SEQ ID NO:17) REV: 3'-GCTA-GAGCGACTACTCCGGCTTTCCGGCTTTAAAGTAG-5'); Rho 266 (SEQ ID NO:18) (FOR: 5'-TCGACA-GAGCGTCTGATGAGCGGTCTTCGGACCGCGAAAG-GAAGTCT GCA-3', (SEQ ID NO:19) REV: 3'-GTCTCG-CAGACTACTCGCCAGAAGCCTG-GCGCTTTCCTTCAG-5'). Short-hairpin RNA (shRNA) cDNA constructs for RNA interference (RNAi) were directionally ligated into the BglII/XhoI sites into pSUPER.puro vector from Oligoengine. The bicistronic Rho-IRES-SEAP vector was created using the internal ribosome entry site of the encephalomyocarditis virus from pIRES2-EGFP vector (Clontech). First, Rho-IRES2-EGFP vector was generated by PCR amplification of full length human Rho cDNA (primer sequences FOR: (SEQ ID NO:20) 5'-AGTATGGTACCA-GAT CTAAGAGTCATCCAGCTGGAG-3'; (SEQ ID NO:21) REV: 5'-GATCGTCGACCTACTGTGTGC-CCCATTC-3') and ligation into the BglII/SalI sites in the multiple cloning region of pIRES2-EGFP (Clontech) upstream of the IRES element. Rho-IRES-SEAP was generated by adding an EcoRI site just downstream of the IRES element in Rho-IRES2-EGFP through a BmgBI/BstXI adapter, and cloning the SEAP cDNA as an EcoRI/MfeI fragment to replace the EGFP cDNA. The SV40 polyA element from the original pIRES2-EGFP vector was used without any modification. pSEAP-STOP-L57Opsin vector was generated by cloning a Rho loop element into (250 region) an XbaI/FseI adapter in the 3'UT of pSEAP2-Control (Clontech) vector. Oligodeoxynucleotides were synthesized by Sigma GenoSys, annealed, and phosphorylated using T4 Polynucleotide Kinase (NEB) prior to ligation into linearized and dephosphorylated vector.

Cell Culture and Transfection. HEK293S.SEAP cells were generated by stable co-transfection of pSEAP2-Control and pTK-Hyg (Clontech) plasmid into HEK293S cells, followed by selection in hygromycin (250 µg/ml). Clonal picks were screened with the SEAP HTS assay (below) and cell lines with different levels of stable SEAP expression and secretion were identified. Clonal picks were screened with the SEAP HTS assay and cell lines with stable SEAP secretion were identified. All HEK293S lines were maintained in Dulbecco's Modified Eagle's Medium/F-12 nutrient mix (DMEM/F12) with 10% (v/v) heat-inactivated calf serum and antibiotics. Cells were grown in 10 cm plates, seeded into 96 well plates and co-transfected (Lipofectamine 2000, InVitrogen) with 500 ng of VAI-Chimera control vector (pUC-VAL) or VAI-hhRz-Chimera constructs and 100 ng of pEGFP-NI plasmid (Clontech) per well. Conditioned culture media was routinely assayed at 72 hours post-transfection unless as otherwise specified. EGFP fluorescence (488 max. excitation/507 max. emission) was measured on an Ascent Fluoroskan FL plate reader (Thermo Corp.) at 485 nm peak excitation/538 nm peak emission (488±7 nm full width half maximum (FWHM)/538±12.5 nm FWHM).

SEAP Assay. Conditioned cell culture media (60 µL) was transferred to separate wells in black-walled 96-well plates (microtest 96-well Optilux Assay plate, BD Falcon #353948) and incubated at 65° C. for 30 min to inactivate non-specific phosphatases. After cooling to room temp, 95 µL of diethanolamine assay buffer (1M diethanolamine, pH 9.8, 1 mM $MgCl_2$, 1 mM L-homoarginine) was added per well, followed by 5 µL of 4-methylumbelliferone (4-MUP) fluorescent substrate to a final concentration of 50 µM per well. SEAP reaction was incubated at room temperature (22° C.) for 1 hr before measuring fluorescence (355 nm max. excitation/460 nm max. emission, which correspond to excitation and emission bands of the fluorescent SEAP reaction product, 4-methyl-umbelliferone) on a Ascent Fluoroskan FL plate reader (355±19 nm FWHM (full with half maximum)/460±12 nm FWHM).

Real-Time Quantitative RT-PCR. Total RNA was purified from transfected cell cultures 48 hours post-transfection with RNeasy kit (Qiagen). Purified RNA was treated with TURBO DNA-free DNAse (Ambion) for 30 min at 37° C. to reduce the potential for contaminating genomic or plasmid DNA and purified a second time using the RNeasy kit. cDNA synthesis was performed using 400 ng of total RNA with the Affinity-Script Reverse Transcriptase system (Stratagene) using the supplied oligo (dT) primers.

Quantitative PCR for human rod opsin (Rho) and hypoxanthine riboxyl transferase (HPRT; exon 6-7) was performed in a Smart Cycler II (Cepheid) thermocycler. Primers that spanned adjacent exons of the respective genes and a probe primer containing a fluorescent dye (FITC) at the 5' end and a quenching dye at the 3' were designed using primer quest software (Integrated DNA Technologies). The PCR primers and probe primers were cDNA specific since the product from cDNA was substantially smaller than the corresponding genomic DNA. Rhodopsin primers (SEQ ID NO:22) (5' AATTTGGAGGGCTTCTTTGCCACC, (SEQ ID NO:23) 5' AGTTGCTCATGGGCTTACACACCA with probe primer 5' (SEQ ID NO:24) 56FAM-AAATTGCCCTGTGGTCCTTG-GTGGT-3BHQ1) and HPRT1 primers (SEQ ID NO:25) (5'GACTTTGCTTTCCTTGGTCAGGCA, (SEQ ID NO:26) 5' GGCTTATATCCAACACTTCGTGGG, probe 5' (SEQ ID NO:27) 56-FAM TCA AGG TCG CAA GCT TGC TGG TGA AA 3'BHQ1) were analyzed on plasmid DNA and genomic DNA to demonstrate their specificity and sensitivity. Quantitative PCR reactions were assembled by mixing equal volumes of PCR primers (0.5 uM) and probe primer (0.25-0.5 uM) with Amplitaq Gold PCR master mix (Applied Biosystems), dispensing into 25 ul reaction tubes and adding 2 ul of the $1^{st}$ strand cDNA sample or plasmid cDNA standard. Thermocycler conditions were 94° C. 6 min followed by 45 cycles at 94° C. (30 sec), 58° C. (15 sec) and 72° C. 30 sec. Fluorescent intensity was measured during the 72° C. extension which for log linear detection of the respective cDNA from 20 pg to 10 ag. Standard samples were analyzed in quadruplicate and $1^{st}$ strand cDNA samples were analyzed in duplicate or triplicate utilizing software provided with the instrument (Cepheid).

Quantitative Analysis. Not all data series for FIG. 2 were normally distributed as determined by Kolmogorov-Smirnov test, so nonparametric analysis of variance was performed using the Kruskal-Wallis test. If the null hypothesis was refuted (all independent variables not equal, criterion of significance: $p<0.05$) then Mann-Whitney tests were used to evaluate differences between the means of samples and controls or between samples. Data for FIG. 3 was normally distributed as determined by Kolmogorov-Smirnov test (null hypothesis: data is normally distributed was not refuted, $p>0.05$). Transfection experiments evaluating hhRz knockdown vs. control plasmid were subject to one-way ANOVA. If the null hypothesis was refuted (all independent variables not equal, p<0.05) then post-hoc t-tests were used to evaluate differences between the means of samples and controls or between samples.

Results. Computational analysis of the full-length SEAP mRNA transcript revealed a highly ordered secondary structure, with rare single-stranded regions. Local structure was rigorously examined under Mfold with 200 nucleotide (nt) folding windows that were moved along the mRNA sequence in 100 nt steps (Patzel, V. and Sczakiel, G. (1998) Nat. Biotechnol. 16, 64-68; Patzel et al. (1999) Nucleic Acids Res. 27, 4328-4334; Scherr, (2000) Nucleic Acids Res. 28, 2455-2461. Within each window an ensemble of structures was generated. Each entry of the ensemble was examined for single stranded regions equal to or greater than 7 nt. The probabilities of such single stranded structures in each ensemble were averaged over all ensemble windows that embraced the candidate target region. Target accessibility was also analyzed with SFold, which uses a Boltzmann-weighted algorithm to sample the entire huge set of potential secondary structures (Ding, Y., Chan, C., and Lawrence, et al. C. (2004) Nucleic Acids Res. 32, W135-W141). The probabilities of accessibility from both MFold and SFold approaches were averaged (FIG. 1). Predicted accessible regions were then examined for potential hhRz target sites (NUH ↓), and a rank order of predicted accessible target sites was determined (Table 1).

TABLE 1

| Target Site | Single-stranded loop size (nt) | MFold Probability (%) | SFold Probability (%) | Average Probability (%) |
|---|---|---|---|---|
| AUA 965 | 8 | 97.50 | 63.40 | 80.00 |
| AUA 1654 | 16 | 80.00 | 72.90 | 76.00 |
| AUC 1260 | 9 | 80.00 | 53.50 | 66.75 |
| CUA 800 | 8 | 50.00 | 72.40 | 61.20 |
| UUA 1707 | 7 | 30.00 | 71.90 | 50.95 |
| AUU 1709 | 7 | 30.00 | 64.90 | 47.45 |
| GUA 755 | 7 | 42.50 | 35.00 | 38.75 |
| AUU 726 | 8 | 17.50 | 55.10 | 36.30 |
| CUC 713 | 8 | 20.00 | 45.80 | 32.90 |
| GUU 150 | 7 | 10.00 | 47.90 | 28.95 |
| CUC 246 | 7 | 10.00 | 36.90 | 23.45 |
| CUU 458 | 12 | 10.00 | 32.40 | 21.20 |

Six candidate hhRz targeting sites were chosen in SEAP mRNA. Five were selected because of their predicted probabilities of accessibility (high: CUA ↓ 800, AUA ↓ 965, AUC ↓ 1260, AUA ↓ 1654 low: GUU ↓ 150) and a sixth ribozyme (low probability) was designed against a site used in a previous study (CUC ↓ 246) (Zakharchuk, et al. Gene 2, 189-193). Ribozyme cDNAs were designed with symmetrical 7 nt antisense flanks surrounding the catalytic consensus core and stabilized for folding by an extended (6 base pair (bp)) Stem II hairpin that was capped by an ultrastable 4 nt UUCG loop (Maksoud, H., Zuker M., Sullivan J. submitted) (Sullivan, J., et al. (2002) Mol. Vis. 8, 102-113) (FIG. 2a). HhRz cDNAs were cloned into a VA1-hhRz expression vector (FIG. 2b). VA1-hhRz constructs permit high level cellular expression by RNA polymerase-III, and target the stable (RNase-resistant) chimeric RNAs to the cytoplasm, where SEAP mRNA, like most other PTGS target RNAs, has its greatest cellular lifetime. Adenoviral VAI RNA normally binds to and inhibits PKR, a cellular protein involved in the interferon response. In the VAI-hhRz chimeras, the central domain is interrupted by a large stem-loop structure to inhibit the action of VAI on PKR (Anderson, et al. (1996) Antimicrob Agents Chemother. 40, 2004-2011). hhRz cDNA constructs are ligated into the large loop (hhRz harbor). The large loop is expected to allow the hhRz to freely access its target without interfering secondary structure interactions with the main body of the VAI RNA Human embryonic kidney cells (HEK293S) (Stillman, B. and Gluzman, Y. (1985) Mol. Cell. Biol. 5, 2051-2060) were engineered to stably express and secrete SEAP (HEK293S.SEAP). A HTS fluorescent assay system for SEAP enzyme activity was developed using purified human placental alkaline phosphatase as model enzyme to simulate secreted extracellular SEAP by HEK293S.SEAP cells. Using the substrate 4-methylumbelliferyl-phosphate (4-MUP), the SEAP assay can detect as little as 1 ng of enzyme in a 150 uL volume of media (120 pmole/L) in a 96-well plate format. 4-MUP is preferable because it is stable at the high pH (9.8) optimum of SEAP enzyme. SEAP converts 4-MUP, which has minimal fluorescence, to 4-methylumbelliferone, which is strongly fluorescent. Using 4-MUP, the dynamic range of measurement was linear for SEAP levels over a 30-fold enzyme concentration range. Stable HEK293S.SEAP cell lines secrete levels of SEAP at the high end of the assay's linear range and at a constant rate over 72 hours. Other fluorescent substrates are available for HTS detection of phosphatase activity. A commonly used phosphatase substrate, dimethylacridinone phosphate, was unable to detect SEAP enzyme activity under alkaline conditions. The sensitivity of the SEAP assay in its current form with 4-MUP as substrate allows miniaturization to a 384-well platform (data not shown).

VA1-hhRz-chimera plasmids were transfected into HEK293S.SEAP cells seeded into 96 well dishes. Media from these cells were assayed 72 hours after transfection. Total secreted SEAP protein was assayed 72 hours after transfection and the mean percent of control VAI-chimera vector SEAP levels are shown±s.e.m. Transfection efficiency was normalized by co-transfection with EGFP. SEAP levels produced fell within the linear dynamic range of the assay. Statistically significant knockdown of SEAP protein levels was found for hhRz 800, hhRz 965, and hhRz 1260, (CUA800, AUA965, and AUC1260 showed 15.97% knockdown, $p=1.41\times10^{-9}$, n=40; 14.36% knockdown, $p=7.89\times10^{-8}$, n=40; and 13.95% knockdown, $p=1.27\times10^{-7}$, n=29 respectively; Kruskal-Wallis analysis of variance $p=9.63\times10^{-14}$) which were three of the four sites predicted to have high accessibility (FIG. 3a).

We chose to further optimize hhRzs targeting the 800 and 965 sites. To determine the extent to which the knockdown observed was related to catalytic function of the hhRzs, single nucleotide mutations were made in the catalytic core (G5C, G8C, and G12C) (Hertel, (1992) Numbering system for the hamet al., Nucleic Acids Res. 20, 3252) and the catalytic inactivated VA1-hhRz expression constructs were retested against active controls. Briefly, inactivating mutations of the two lead candidate hhRz-VAI constructs were generated by a single G→C mutation of the G5, G8, or G12 positions in the consensus catalytic core (Eckstein, et al. (2001) Chembiochem. 2, 629-635; Roychowdhury-Saha, (2006) RNA 12, 1-7). Mean percent of control vector SEAP levels are shown±s.e.m in FIG. 3b. None of the catalytic mutations showed a significant reversal in knockdown compared to their active hhRz versions [15.97% knockdown for SEAP 800 active hhRz (n=40) compared to: 11.98% knockdown for SEAP 800 G5C (n=8, p=0.49), 12.44% knockdown for SEAP 800 G8C (n=8, p=0.56), and 16.47% knockdown for SEAP 800 G12C (n=15, p=0.34); 14.36% knockdown for SEAP 965 active hhRz (n=40) compared to: 14.72% knockdown for SEAP 965 G5C (n=16, p=0.41), 20.35% knockdown for SEAP 965 G8C (n=24, p=0.03), and 21.83% knockdown for SEAP 965 G12C (n=24, p=0.10)] (FIG. 3b). This suggests that the knockdown of SEAP protein by the active ribozymes is due to antisense or catalytic antisense effects rather than a pure catalytic effect. Identical outcomes were found with 6 bp Stem-II UUCG hhRzs targeting human rod opsin (data not shown). We examined whether the extension of stem II to 6 bp in our standard hhRz design affected intracellular catalytic activity. While the extended 6 bp ribozyme was designed to stabilize the formation of the correct secondary structure in vitro, in a cellular environment, the classical 4 bp stem II design increased the level of SEAP protein knockdown, and single base G12C mutations completely reversed this knockdown (FIG. 3c).

We then analyzed potential enhancements to optimize the lead 965 hhRz candidate. The catalytic core of the hhRz is already evolutionarily optimized (Ishizaka, et al. (1995) Biochem. Biophys. Res. Commun. 214, 403-409; Tang, J. and Breaker, R. (1997) RNA 3, 914-925; Salehi-Ashtiani, K. (2001) Nature 414, 82-84; Eckstein, et al. (2001) Chembiochem. 2, 629-635). Recent studies indicate that the ability of hhRz RNAs to form catalytically active conformations in physiological levels of intracellular $Mg^{2+}$ relates to a natural pseudoknot interaction between bases in stem I and stem II that were deleted from most trans hhRz cleavage studies over the last decade (De la Pena, et al. (2003) EMBO J. 22, 5561-70; Khvorova, et al. (2003) Nat. Struct. Biol. 9, 708-712; Penedo, et al. (2004) RNA 10, 880-888; Martick, M. and Scott, W. (2006) Cell 6, 1-12). Inserting natural hhRz sequences in cis in the 3'UTR of SEAP mRNA confirmed the drastic difference in the ability of natural hhRz sequences containing stem I loop sequences to knockdown gene expression compared to the minimal hhRz lacking a stem I loop. We tested the ability of translating these observations for enhancing trans hhRz cleavage by modifying the 965 minimal hhRz sequences with a Stem I bulge sequence and a Stem II loop sequence derived from the natural sequence found in Peach Latent Mosaic Virus (PLMVd) hhRz (Saksmerprome, V., et al. (2004) RNA 10, 1916-24; Roychowdhury-Saha, (2006) RNA 12, 1-7; Burke, D. and Greathouse, S. (2005) BMC Biochem. 6, 14). The modified PLMVd hhRz showed enhanced knockdown compared to our 6 bp stabilized hhRz construct, but no significant enhancement over the classic 4 bp minimal hhRz design. A single base mutation at the G12 position (G12C) of the catalytic core significantly reduced the level of knockdown indicating that knockdown rises from catalytic activity (FIG. 3c). We were not able to translate the drastic improvement in catalytic ability seen in cis hhRz constructs to a trans hhRz construct, thus demonstrating the need for in vivo testing.

Example 2

This Example demonstrates screening test ribozymes and test RNAi agents for activity against a target mRNA sequence in a bicistronic RNA. Also demonstrated is an example of providing less than a complete mRNA sequence as the target mRNA sequence.

We chose a model mRNA target, human rod opsin mRNA for including in the bicistronic mRNA. This mRNA codes for rhodopsin, the visual pigment of scotopic range phototransduction. The opsin gene is the site of a large number (>125) of mutations that cause three classes of retinal disease (autosomal dominant RP, autosomal recessive RP, autosomal dominant congenital stationary night blindness). Human rod opsin mRNA is an average sized mRNA (1.8 kB dominant photoreceptor transcript), is moderately abundant, is slightly GC rich (56.6%), is quite stable in mammalian photoreceptors and spends most of its lifetime in the cytoplasm (Nathans J and Hogness D. S. (1984) Proc. Natl. Acad. Sci. USA 81: 4851-4855). There are hundreds of hhRz NUH ↓ cleavage motifs in any moderate sized mRNA target and 236 potential cleavage sites in the dominantly expressed full-length human rod opsin mRNA (Nathans J and Hogness D. S. (1984) Proc. Natl. Acad. Sci. USA 81: 4851-4855). We tabulated regions that contain ss platforms greater than or equal to 8 nt. Examples of discrete structural state outputs from MFold (there were 1088 images analyzed) that show large ss loops or hybridized stem structures were identified. Initial Mfold local structural state analysis suggested large stable ss loops in regions embracing 250, 1190, and 1410. A small stable loop was identified also at region 780. A hybridized stem structure at 350 was selected from many possibilities as a control. In different regions there was substantial number of different substrates that contained a ss platform such that a probability of the dominant substate could be determined. The probability of the dominant substate in these regions was determined by Mfold analysis. SFold output in these general regions was also determined and varies extensively across the entire mRNA. The regions presenting stable ss loops in local secondary structures had substantial access probabilities, varying over primary sequence spans consistent with the size of the ss loops seen in Mfold analysis, whereas the control hybridized region had low probability. OligoWalk output across the entire mRNA shows regions of high (relatively unstable) and low (relativey stable).

The SEAP HTS assay was employed to test several hhRzs targeted to cleave human rod opsin mRNA. We used the SEAP HTS platform in two ways to test cleavage of Rho mRNA. First, the bicistronic vector (pRho-IRES-SEAP) was designed utilizing an internal ribosome entry site (IRES) sequence to produce a single mRNA transcript that is able to express both Rho and SEAP proteins. The full length Rho cDNA was placed upstream of the IRES sequence with the SEAP cDNA downstream. The sequence of pRho-IRES-SEAP is provided as (SEQ ID NO:1. In SEQ ID NO:1, positions 1-33 are vector sequence between a cytomegalovirus (CMV) transcription start and RHO transcript start. The following 1501 nucleotides are RHO cDNA sequence, followed by 12 nucleotides of linker sequence, followed by 591 nucleotides of ECMV IRES sequence, followed by a 1,663 nucleotide SEAP coding sequence, and a final 95 nucleotides of SV40 poly A signal. The rationale is that since RNAs fold into stable secondary structures during transcription (Tinoco, I. and Bustamante, C. (1999) J. Mol. Biol. 293, 271-281) that an upstream disease target is more likely to accurately represent the structure of the native mRNA for testing PTGS agents. HhRzs targeted to SEAP or Rho were tested for their independent ability to knockdown SEAP expression. This method provides a sensitive and efficient measure of hhRz cleavage within either the Rho or SEAP elements of the bicistronic mRNA. In this way, any arbitrary mRNA target could be analyzed with the a secretable reporter protein by placing the full length cDNA upstream of the IRES element in this engineered plasmid construct. We used a ribozyme we previously determined to be active against Rho (site 725) and the SEAP 965 hhRzs and co-transfected them as VAI-Chimera constructs together with the bicistronic Rho-IRES-SEAP plasmid into HEK293S cells. SEAP expression was assayed relative to control transfection 48 hours post-transfection.

For the results presented in FIG. 4a, vector was generated with the full length Rho cDNA placed upstream of the IRES sequence and the SEAP cDNA downstream. As RNA folds during transcription, placing the target mRNA upstream of the reporter acts to favor unbiased folding of the target mRNA (Tinoco, I. and Bustamante, C. (1999) J. Mol. Biol. 293, 271-281). VAI-hhRzs targeting Rho (725) and SEAP (965) (in pUC-VAL) were transiently co-transfected into HEK-293S cells with the pRho-IRES-SEAP construct. Media was removed 48 hours post-transfection and assayed for SEAP protein expression. Both hhRz targeting Rho and SEAP showed significant protein knockdown (11.52% knockdown for Rho725, $p=3.64\times10^{-4}$; 22.95% and 16.85% knockdown for SEAP965, $p=1.72\times10^{-10}$) (One-way ANOVA F=39.0, $p=3.98\times10^{-10}$, n=3).

Both active hhRzs targeting Rho and SEAP showed significant reductions in SEAP activity 48 hours post-transfection, with catalytic inactive mutants targeted to these same sites reversed the knockdown effect (FIG. 4a).

pSUPER shRNA vectors were designed to target the same sites targeted by the hhRzs (Rho 725 and SEAP 965) and co-transfected with Rho-IRES-SEAP. The shRNA constructs were transiently co-transfected with pRho-IRES-SEAP plasmid into HEK 293S cells. Media was removed 48 hours post-transfection and assayed for SEAP activity. Total RNA was then extracted and Rho mRNA levels quantified by qRT-PCR. Both shRNA constructs reduced SEAP protein activity and Rho mRNA levels, with a rough correlation between the SEAP protein activity relative to Rho mRNA levels (FIG. 4). Specifically, both SEAPi965 and Rhoi725 showed significant SEAP protein knockdown relative to scramble control (One-way ANOVA F=1035.78, p=0, n=9), with a 62.15% knockdown in SEAP activity for SEAPi965 ($p=1.71\times10^{-18}$) and a 19.61% knockdown in SEAP activity for Rhoi725 ($p=2.40\times10^{-9}$). Corresponding Rho mRNA levels were also significantly decreased relative to scramble control (one-way ANOVA F=60.01, $p=4.59\times10^{-10}$, n=9) with a 68.62% knockdown for SEAPi965 ($p=1.81\times10^{-8}$) and a 37.47% knockdown for Rhoi725 ($p=1.41\times10^{-4}$).

Figure 6A:
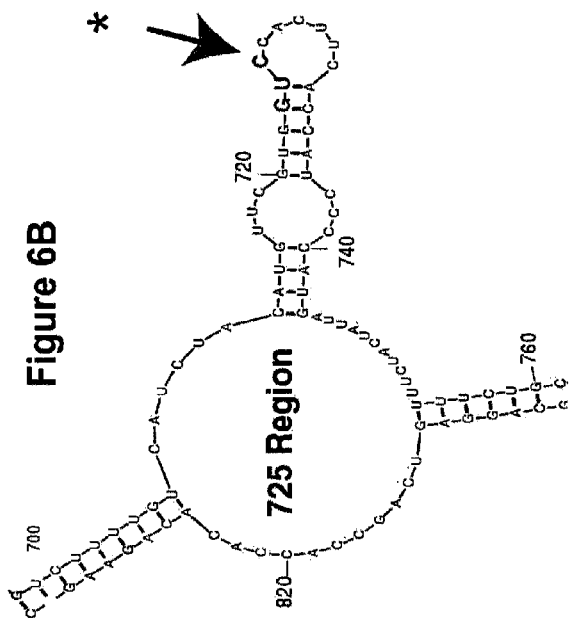
FIG. 6a provides a graphical representation of expected structures around the 250 nucleotide region of Rho which is shown as SEQ ID NO:38.
Figure 6B:
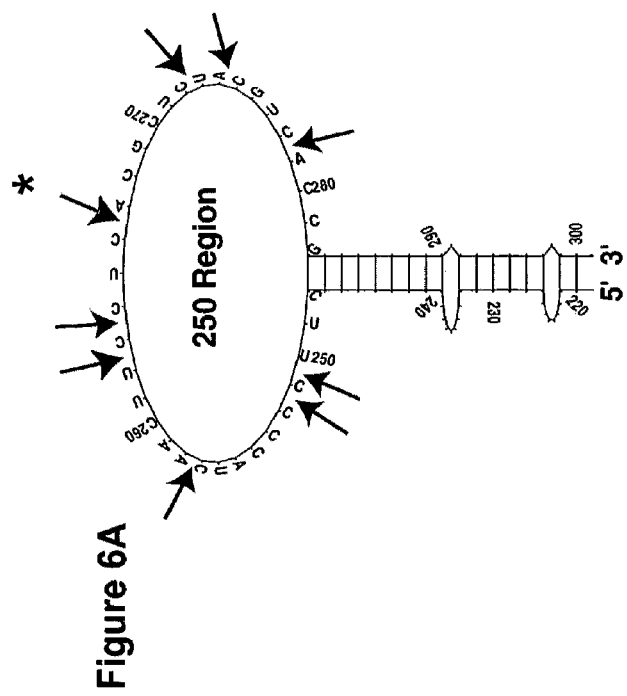
FIG. 6b provides a graphical representation of expected structures around the 725 nucleotide region of Rho which is shown as SEQ ID NO:39.
Figure 6C:
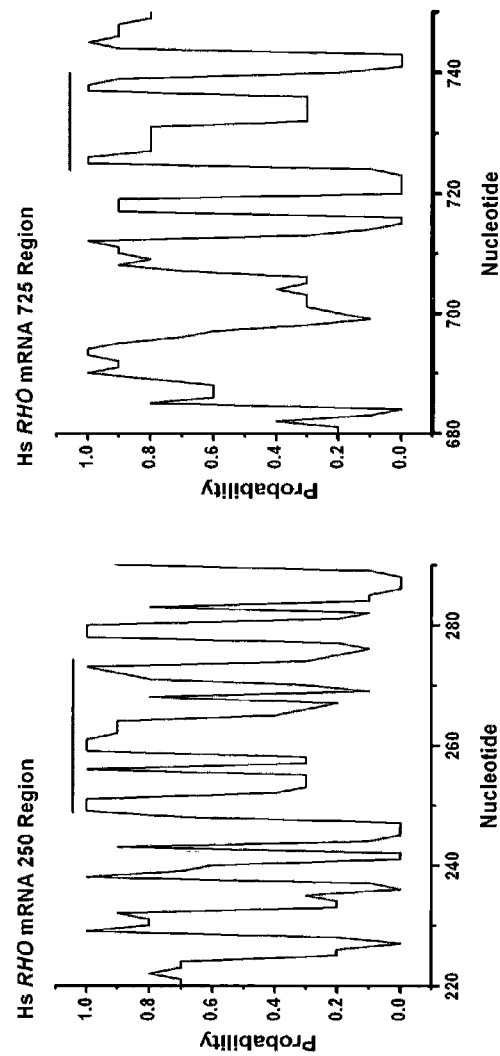
FIG. 6c provides Mfold P-num graphs for each of the 250 and 725 regions of Rho.

Shown in FIGS. 6a and 6b are expected structures around the 250 and 725 regions of Rho. The * arrows show the cleavage sites at 266 and 725. Note the large single stranded regions in the region in which the ribozyme must attack and anneal. P-num graphs for each of the 250 and 725 regions are provided in FIG. 6c.

Figure 5:
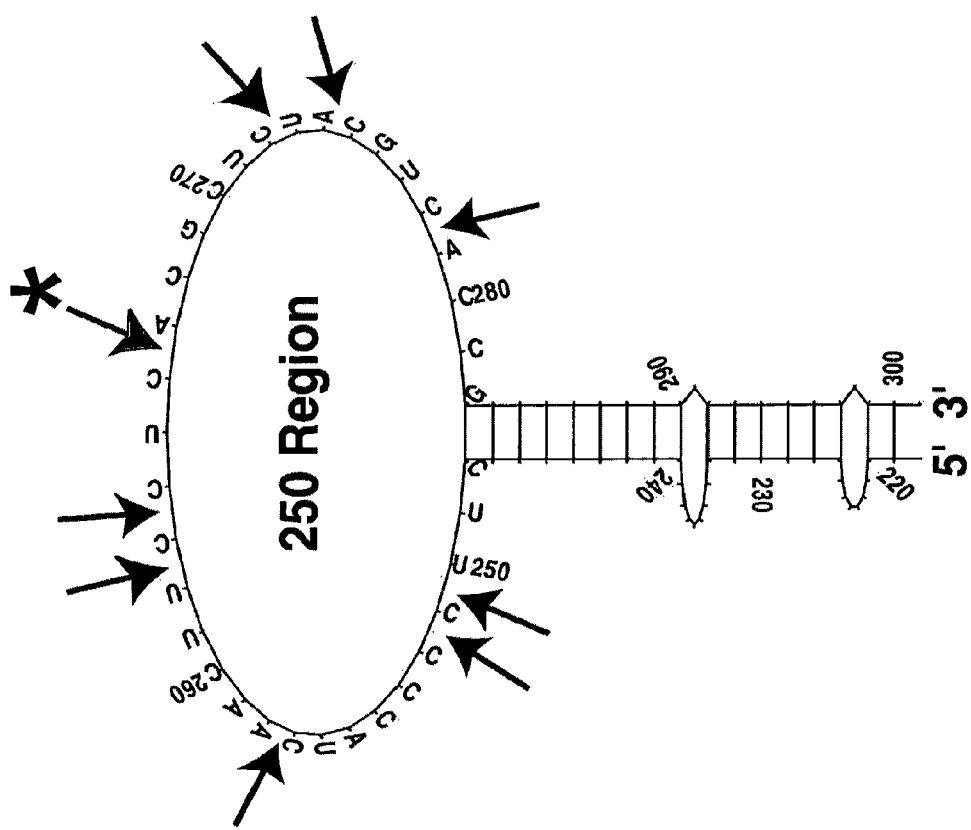
FIG. 5 provides a graphical representation of a predicted large stem loop in the region around nt 250 in human rod opsin mRNA. A cleavage site (CUC↓-266) in the single-stranded region (nucleotides 281-315 of SEQ ID NO:1) was successfully targeted by a hhRz cloned into a vector termed pG-VAL. This stem loop structure is shown with all potential hhRz cleavage sites (black arrows) and the CUC↓-hhRz cleavage site labeled (arrow*).

The second method of testing the hhRz platform was based on computational analysis of the target mRNA to identify stable secondary structures with large single stranded elements that present suitable platform for PTGS ligand annealing. The region that is targeted by Rho266 hhRz is a potentially large loop (33 nucleotides) capping a stable stem structure (FIG. 4b; FIG. 5). A 62 nucleotide cDNA coding for this specific secondary structure of human rod opsin mRNA was ligated into the early 3'UT of the SEAP expression vector between a set of engineered restriction sites. This construct was transiently co-transfected with hhRzs targeting Rho (266) or SEAP (965) or control vector. Both hhRz constructs reduced SEAP protein levels by about 40% (36.37% knockdown for the SEAP 965 construct (p=0.005, n=16) and 34.98% knockdown for the Rho 266 construct ($p=3.54\times10^{-4}$, n=16) (One-way ANOVA F=10.0, $p=2.60\times10^{-4}$). Thus, any hhRz targeting opsin mRNA in this predicted stem-loop, or in any expected stable stem-loop, bulge loop, or multibranch loop structure could be tested in this HTS system. Further, it is expected that any target mRNA sequence could be detected in this system.

Example 3

This Example provides a demonstration of in silico comparison of computational analysis of folding for three distinct bicistronic mRNAs (human RHO-IRES-SEAP, mouse RPE65-IRES-SEAP, and mouse RDH5-IRES-SEAP) that can be used as dicistronic RNA in the method of the invention. The sequences of the RPE65-IRES-SEAP, and mouse RDH5-IRES-SEAP are provided as SEQ ID NO:28 and SEQ ID NO:29, respectively. The mouse RPE65 full length mRNA is provided in the first 1821 nucleotides of SEQ ID NO:28, followed by the ECMV IRES, SEAP cDNA and polyA signal provided by the vector. The mouse RDH5 full length mRNA is provided in the first 1,233 nucleotides of SEQ ID NO:29, and the remaining sequence is as for the RPE65 construct.

In developing the use of dicistronic mRNA as a target for screening of agents that could reduce the level of a target mRNA in a cell, we considered the possibility that the strong secondary and tertiary structure of IRES (internal ribosome entry site), which is placed between the upstream target RNA and the downstream SEAP reporter RNA, could provide an insulator module that minimizes potential misfolding of the target RNA component due to the presence of other components in the dicistronic fusion mRNA. In order to test this, we used MFold to fold three dicistronic mRNAs (human RHO-IRES-SEAP, mouse RPE65-IRES-SEAP, and mouse RDH5-IRES-SEAP). MFold seeks the minimum free energy conformation (most stable) and explores all possible base pairings to do so regardless of where they are located in the mRNA. It is well known that RNA folding occurs co-transcriptionally as the RNA polymerase is moving along the template. For this reason, we placed the target sequences at the 5' end (upstream) in the dicistronic mRNA in order to bias correct folding of this important part of the dicistronic mRNA for proper and successful screening. On the other hand, MFold does not account for the known biology of RNA folding. Therefore, folding a dicistronic mRNA under MFold creates the statistically worst possible situation for investigating the impact of other sequences (IRES, SEAP) on the folding of target (RHO, RPE65, RDH5).

One of the outputs of MFold is p-num, which shows the number of other nucleotides that any given nucleotide forms base pairs with in the entire set of MFold structures (minimum folding energy (MFE) and less stable structures). Nucleotides with a large number of partners suggests that that a particular nucleotide is more likely to be single stranded, whereas a nucleotide with few or no partners is more likely to be stably base paired. The P-num variable along the nucleotide sequence of an mRNA then generates a map that allows comparison of the entire dicistronic mRNAs with only the target components for which it is desired to preserve folding integrity.

Figure 7:
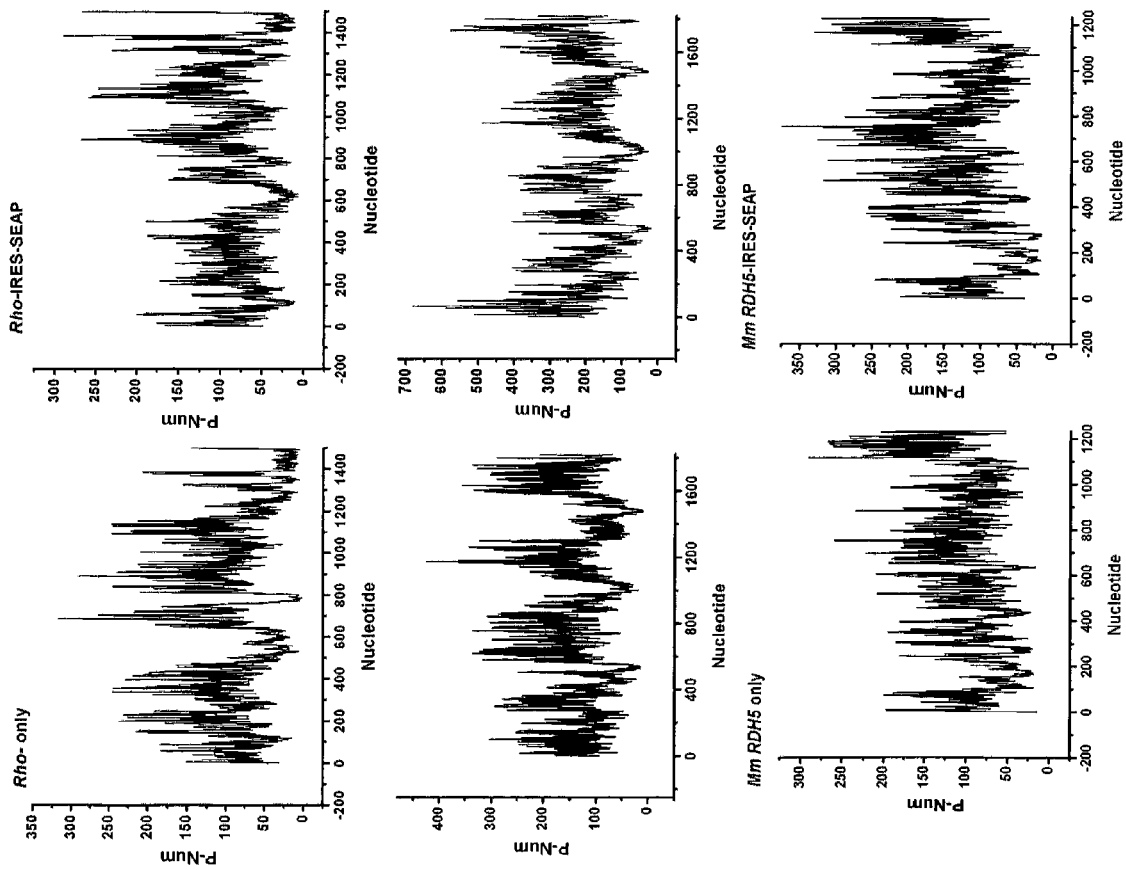
FIG. 7 provides a graphical representation of in silico comparisons of computational analysis of folding for three distinct bicistronic mRNAs (human RHO-IRES-SEAP, mouse RPE65-IRES-SEAP, and mouse RDH5-IRES-SEAP). The graphs provide summaries of MFold p-num data, which shows the number of other nucleotides that any given nucleotide forms base pairs with in the entire set of MFold structures (minimum folding energy (MFE) and less stable structures) which demonstrate little to no change when the three dicistronic RNAs from FIG. 6 are folded independently or when folded as the central component of a much larger Target-IRES-SEAP dicistronic mRNA.

In all cases of P-Num maps shown in FIG. 7, the full region of the isolated Target RNA is shown in the left panel and the same corresponding region of the Target-IRES-SEAP P-Num map is shown in the right panel (the Target-IRES-SEAP P-Num map is much larger). Only the relevant portions of the target and the target in the dicistronic mRNA are compared. Note the similarity of the P-Num maps for all three dicistronic mRNAs. This evidence indicates, even in the worst case scenario with MFold, that the Target elements are folding independently of the other component of the dicistronic mRNAs.

Figure 8:
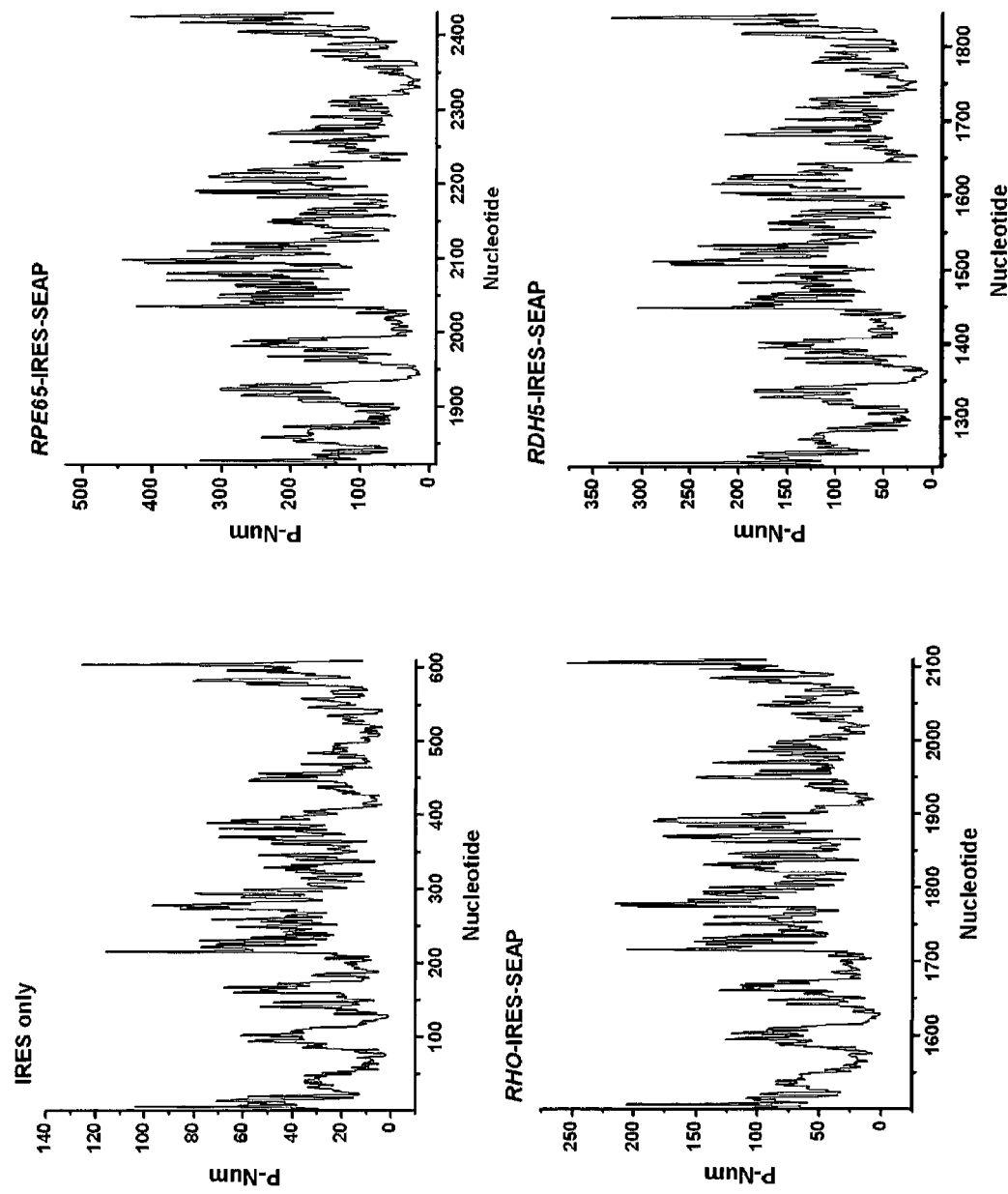
FIG. 8 provides graphical representations of P-Num maps showing that the IRES component of the Target-IRES-SEAP dicistronic mRNA for three independent dicistronic target mRNAs has very similar P-Num maps. This indicates that IRES folding serves as an insulator between upstream target and downstream reporter domains.

If IRES is an insulator element, then its P-Num map should demonstrate little to no change when the sequence is folded independently or when it is folded as the central component of a much larger Target-IRES-SEAP dicistronic mRNA. Shown in FIG. 8 is just such a comparison. The IRES component of the Target-IRES-SEAP dicistronic mRNA for three independent dicistronic target mRNAs has very similar P-Num maps. This strongly suggests that IRES is an insulator module, isolating the upstream target component from the downstream reporter component in each dicistronic mRNAs tested. Thus, the use of dicistronic constructs as disclosed herein has significantly improved utility for identifying polynucleotide agents that can cause a reduction of a target mRNA in a cell.

While specific examples have been presented herein, those skilled in the art will recognize that routine modifications can be made to the invention as described herein and these modifications are intended to be within the scope of the invention.

We claim:

1. A method for identifying a test polynucleotide that can reduce the level of a target mRNA comprising the steps of:
   i) providing cells expressing an RNA polynucleotide comprising a target mRNA sequence, a single internal ribosome entry sequence (IRES) and a sequence encoding a secreted reporter protein, wherein the single IRES is 3' to the target mRNA sequence and 5' to the sequence encoding the secreted reporter protein;
   ii) introducing to the cell a test polynucleotide, and
   iii) measuring activity of the secreted reporter protein;
   wherein a reduction in secreted reporter protein activity relative to a control cell expressing an RNA polynucleotide comprising the target mRNA sequence, the single IRES and the sequence encoding the secreted reporter protein into which the test polynucleotide has not been introduced is indicative that the test polynucleotide is capable of reducing the level of the target mRNA in the cells.

2. The method of claim 1, wherein the test polynucleotide is selected from the group consisting of a hammerhead ribozyme (hhRz), an antisense RNA, a small interfering RNA (siRNA), a DNAzyme, a hairpin ribozyme, and a Hepatitis Delta Virus ribozyme.

3. The method of claim 1, wherein the RNA polynucleotide comprising the target mRNA sequence, the IRES and the sequence encoding the secreted reporter protein is expressed from a DNA expression vector that has been transfected into the cell.

4. The method of claim 2, wherein the hhRz, antisense RNA or the siRNA is expressed from a DNA expression vector that has been transfected into the cell.

5. The method of claim 1, wherein the secreted reporter protein is selected from the group consisting of chloramphenicol acetyl transferase, β-galactosidase, Green Fluorescent Protein (GFP), Enhanced Green Fluorescent Protein, luciferase, a luciferase-GFP fusion protein, and secreted placental alkaline phosphatase (SEAP).

6. The method of claim 5, wherein the secreted reporter protein is SEAP.

7. The method of claim 1, wherein the single IRES is an Encephalomyocarditis virus IRES.

8. The method of claim 1, further comprising prior to performing step ii) analyzing the nucleotide sequence of the target mRNA to predict a location of a single stranded region of the target mRNA.

9. The method of claim 8, wherein analyzing the nucleotide sequence of the target mRNA is performed using a computer program.

10. The method of claim 8, wherein the single stranded region of the target mRNA comprises a hammerhead ribozyme cleavage site.

11. The method of claim 1, wherein the cells are divided into a plurality of reactions, and wherein steps ii) and iii) are performed with a distinct test polynucleotide in each reaction chamber.

12. The method of claim 1, wherein the target mRNA sequence comprises a sequence encoding a complete protein.

* * * * *

```
                         SEQUENCE LISTING

<160> NUMBER OF SEQ ID NOS: 39

<210> SEQ ID NO 1
<211> LENGTH: 3901
<212> TYPE: RNA
<213> ORGANISM: artificial sequence
<220> FEATURE:
<223> OTHER INFORMATION: Rho-IRES-SEAP fusion mRNA

<400> SEQUENCE: 1
ucagauccgc uagcgcuacc ggacucagau cuaagaguca uccagcugga gcccugagug      60
gcugagcuca ggccuucgca gcauucuugg gugggagcag ccacggguca gccacaaggg     120
ccacagccau gaauggcaca gaaggcccua acuucuacgu gcccuucucc aaugcgacgg     180
gugugguacg cagccccuuc gaguaccacc aguacuaccu ggcugagcca uggcaguucu     240
ccaugcuggc cgccuacaug uuucugcuga ucgugcuggg cuuccccauc aacuuccuca     300
cgcucuacgu caccguccag cacaagaagc ugcgcacgcc ucucaacuac auccugcuca     360
accuagccgu ggcugaccuc uucaugaucc uagguggcuu caccagcacc cucuacaccu     420
cucugcaugg auacuucguc uucgggccca caggaugcaa uuggaggc uucuuugcca     480 cccugggcgg ugaaauugcc cugugguccu ggugguccu ggccaucgag cgguacgugg     540
uggugaguaa gcccaugagc aacuuccgcu ucgggagaa ccaugccauc augggcguug     600
ccuucaccug ggucauggcg cuggccugcg ccgcaccccc acucgccggc uggccaggu     660 acaucccga gggccugcag ugcucgugug gaaucgacua cuacacgcuc aagccggagg     720
ucaacaacga gucuuugguc aucuacaugu ucguggucca cuuccaucc cccaugauua     780 ucaucuuuuu cugcuaugg cagcucgucu ucaccgucaa ggaggccgcu gcccagcagc     840
aggagucagc caccacacag aaggcagaga aggaggucac ccgcaugguc aucaucaugg     900
ucaucgcuuu ccugaucgc ugggugcccu acgccagcgu ggcauucuac aucuucaccc     960
accagggcuc caacuucggu cccaucuuca ugaccauccc agcguucuuu gccaagagcg    1020
ccgccaucua caacccuguc aucuauauca ugaugaacaa gcaguuccgg aacugcaugc    1080
ucaccaccau cugcugcggc aagaacccac ugggugacga ugaggccucu gcuaccgugu    1140
ccaagacgga gacgagccag guggccccgg ccuaagaccu gccuaggacu cugugggcga    1200
cuauaggcgu cucccaaucc cuacaccuuc ccccagccac agccauccca ccaggagcag    1260
cgccugugca gaaugaacga agucacauag gcuccuuaau uuuuuuuuu uuuuuaagaa    1320 auaauuaaug aggcuccuca cucaccuggg acagccugag aagggacauc caccaagacc    1380
uacugaucug gagucccacg uucccaagg ccagcggau gugugcccu ccuccuccca    1440 acucaucuuu caggaacacg aggauucuug cuuucuggaa aaguguccca gcuuagggau    1500
aaguguccag cacagaaugg ggcacacagu aggucgacgg uaccgcgggc ccgggauccg    1560
cccucucccc ucccccccc cuaacguuac uggccgaagc cgcuuggaau aaggccggug    1620
ugcguuuguc uauaugauau uuuccaccau auugccgucu uuuggcaaug ugagggcccg    1680
gaaaccuggc ccugucuucu ugacgagcau uccuaggggu cuuccccuc ucgccaaagg    1740 aaugcaaggu cuguugaaug ucgugaagga agcaguuccu cuggaagcuu cuugaagaca    1800
```

-continued

| | |
|---|---|
| aacaacgucu guagcgaccc uuugcaggca gcggaacccc ccaccuggcg acaggugccu | 1860 |
| cugcggccaa aagccacgug uauaagauac accugcaaag gcggacaac cccagugcca | 1920 |
| cguugugagu uggauaguug uggaaagagu caaauggcuc uccucaagcg uauucaacaa | 1980 |
| ggggcugaag gaugcccaga agguacccca uuguauggga ucugaucugg ggccucgguu | 2040 |
| cacaugcuuu acauguguuu agucgagguu aaaaaaacgu cuaggccccc cgaaccacgg | 2100 |
| ggacgugguu uccuuugaa aaacacgaug auaauauggc caccgcccac caugcugcug | 2160 |
| cugcugcugc ugcugggccu gaggcuacag cucucccugg gcaucauccc aguugaggag | 2220 |
| gagaacccgg acuucuggaa ccgcgaggca gccgaggccc ugggugccgc caagaagcug | 2280 |
| cagccugcac agacagccgc caagaaccuc aucaucuucc ugggcgaugg gauggggug | 2340 |
| ucuacgguga cagcugccag gauccuaaaa gggcagaaga aggacaaacu ggggccugag | 2400 |
| auaccccugg ccauggaccg cuucccauau guggcucugu ccaagacaua caauguagac | 2460 |
| aaacaugugc cagacagugg agccacagcc acgccuacc ugugcggggu caagggcaac | 2520 |
| uuccagacca uuggcuugag ugcagccgcc cgcuuuaacc agugcaacac gacacgcggc | 2580 |
| aacgagguca ucuccgugau gaaucgggcc aagaaagcag ggaagucagu gggaguggua | 2640 |
| accaccacac gagugcagca cgccucgcca gccggcaccu acgcccacac ggugaaccgc | 2700 |
| aacugguacu cggacgccga cgugccugcc ucggcccgcc aggaggggug ccaggacauc | 2760 |
| gcuacgcagc ucaucuccaa cauggacauu gacgugaucc uagguggagg ccgaaaguac | 2820 |
| auguuucgca ugggaacccc agaccccgag uacccagaug acuacagcca agguggggacc | 2880 |
| aggcuggacg ggaagaaucu ggugcaggaa uggcuggcga agcgccaggg ugcccggguau | 2940 |
| gugugggaacc gcacgagcu caugcaggcu cccuggaccc cgucugugac ccaucucaug | 3000 |
| ggucucuuug agccuggaga caugaaauac gagauccacc gagacuccac acuggacccc | 3060 |
| ucccugaugg agaugacaga ggcugcccug cgccugcuga gcaggaaccc ccgcggcuuc | 3120 |
| uuccucuucg uggagggugg ucgcaucgac cauggucauc augaaagcag ggcuuaccgg | 3180 |
| gcacugacug agacgaucau guucgacgac gccauugaga gggcgggcca gcucaccagc | 3240 |
| gaggaggaca cgcugagccu cgucacugcc gaccacuccc acgucuucuc cuucggaggc | 3300 |
| uaccccugc gagggagcuc caucuucggg cuggcccug gcaaggcccg ggacaggaag | 3360 |
| gccuacacgg uccuccuaua cggaaacggu ccaggcuaug cucaaggga cggcgcccgg | 3420 |
| ccggauguua ccgagagcga gagcgggagc cccgaguauc ggcagcaguc agcagugccc | 3480 |
| cuggacgaag agaccacgc aggcgaggac guggcggugu cgcgcgcgg cccgcaggcg | 3540 |
| caccugguuc acggcgugca ggagcagacc uucauagcgc acgucauggc cuucgccgcc | 3600 |
| ugccuggagc ccuacaccgc cugcgaccug gcgcccccg ccggcaccac cgacgccgcg | 3660 |
| caccccgggu acucuagagu cgauaucggg gcggccggcc gcuucgagca gacaugauaa | 3720 |
| gauacauuga ugaguuugga caaccacaa cuagaaugca gugaaaaaaa ugcuuuauuu | 3780 |
| gugaaauuug ugaugcuauu gcuuucaauu guuguuguua acuuguuuau ugcagcuuau | 3840 |
| aaugguuaca aauaaagcaa uagcaucaca aauuucacaa auaaagcauu uuuuucacug | 3900 |
| c | 3901 |

<210> SEQ ID NO 2
<211> LENGTH: 50
<212> TYPE: DNA
<213> ORGANISM: artificial sequence
<220> FEATURE:
<223> OTHER INFORMATION: ribozyme

<400> SEQUENCE: 2
tcgaccctcc tcctgatgag cggtcttcgg accgcgaaac tgggtctgca          50

<210> SEQ ID NO 3
<211> LENGTH: 42
<212> TYPE: DNA
<213> ORGANISM: artificial sequence
<220> FEATURE:
<223> OTHER INFORMATION: ribozyme

<400> SEQUENCE: 3
gggaggagga ctactcgcca gaagcctggc gctttgaccc ag          42

<210> SEQ ID NO 4
<211> LENGTH: 50
<212> TYPE: DNA
<213> ORGANISM: artificial sequence
<220> FEATURE:
<223> OTHER INFORMATION: ribozyme

<400> SEQUENCE: 4
tcgacagatg atctgatgag cggtcttcgg accgcgaaag gttctctgca          50

<210> SEQ ID NO 5
<211> LENGTH: 42
<212> TYPE: DNA
<213> ORGANISM: artificial sequence
<220> FEATURE:
<223> OTHER INFORMATION: ribozyme

<400> SEQUENCE: 5
gtctactaga ctactcgcca gaagcctggc gctttccaag ag          42

<210> SEQ ID NO 6
<211> LENGTH: 50
<212> TYPE: DNA
<213> ORGANISM: artificial sequence
<220> FEATURE:
<223> OTHER INFORMATION: ribozyme

<400> SEQUENCE: 6
tcgacttggc tgctgatgag cggtcttcgg accgcgaaag tcatcctgca          50

<210> SEQ ID NO 7
<211> LENGTH: 42
<212> TYPE: DNA
<213> ORGANISM: artificial sequence
<220> FEATURE:
<223> OTHER INFORMATION: ribozyme

<400> SEQUENCE: 7
gaaccgacga ctactcgcca gaagcctggc gctttcagta gg          42

<210> SEQ ID NO 8
<211> LENGTH: 50
<212> TYPE: DNA
<213> ORGANISM: artificial sequence
<220> FEATURE:
<223> OTHER INFORMATION: ribozyme

<400> SEQUENCE: 8
tcgacgatct cgctgatgag cggtcttcgg accgcgaaat ttcatctgca          50

```
<210> SEQ ID NO 9
<211> LENGTH: 42
<212> TYPE: DNA
<213> ORGANISM: artificial sequence
<220> FEATURE:
<223> OTHER INFORMATION: ribozyme

<400> SEQUENCE: 9
gctagagcga ctactcgcca gaagcctggc gctttaaagt ag                42

<210> SEQ ID NO 10
<211> LENGTH: 50
<212> TYPE: DNA
<213> ORGANISM: artificial sequence
<220> FEATURE:
<223> OTHER INFORMATION: ribozyme

<400> SEQUENCE: 10
tcgacgcccg aactgatgag cggtcttcgg accgcgaaat ggagcctgca        50

<210> SEQ ID NO 11
<211> LENGTH: 42
<212> TYPE: DNA
<213> ORGANISM: artificial sequence
<220> FEATURE:
<223> OTHER INFORMATION: ribozyme

<400> SEQUENCE: 11
gcgggcttga ctactcgcca gaagcctggc gctttacctc gg                42

<210> SEQ ID NO 12
<211> LENGTH: 50
<212> TYPE: DNA
<213> ORGANISM: artificial sequence
<220> FEATURE:
<223> OTHER INFORMATION: ribozyme

<400> SEQUENCE: 12
tcgacatcaa tgctgatgag cggtcttcgg accgcgaaat cttatctgca        50

<210> SEQ ID NO 13
<211> LENGTH: 42
<212> TYPE: DNA
<213> ORGANISM: artificial sequence
<220> FEATURE:
<223> OTHER INFORMATION: ribozyme

<400> SEQUENCE: 13
gtagttacga ctactcgcca gaagcctggc gctttagaat ag                42

<210> SEQ ID NO 14
<211> LENGTH: 56
<212> TYPE: DNA
<213> ORGANISM: artificial sequence
<220> FEATURE:
<223> OTHER INFORMATION: primer sequence

<400> SEQUENCE: 14
tcgacgtgga taatctcgct gatgagtcgc tgggatgcga cgaaatttca tctgca    56

<210> SEQ ID NO 15
<211> LENGTH: 48
<212> TYPE: DNA
<213> ORGANISM: artificial sequence
<220> FEATURE:
<223> OTHER INFORMATION: ribozyme cDNA
```

```
<400> SEQUENCE: 15
gcacctatta gagcgactac tcagcgaccc tacgctgctt taaagtag          48

<210> SEQ ID NO 16
<211> LENGTH: 46
<212> TYPE: DNA
<213> ORGANISM: artificial sequence
<220> FEATURE:
<223> OTHER INFORMATION: ribozyme cDNA

<400> SEQUENCE: 16
tcgacgatct cgctgatgag gccgaaaggc cgaaatttca tctgca            46

<210> SEQ ID NO 17
<211> LENGTH: 38
<212> TYPE: DNA
<213> ORGANISM: artificial sequence
<220> FEATURE:
<223> OTHER INFORMATION: ribozyme cDNA

<400> SEQUENCE: 17
gctagagcga ctactccggc tttccggctt taaagtag                     38

<210> SEQ ID NO 18
<211> LENGTH: 50
<212> TYPE: DNA
<213> ORGANISM: artificial sequence
<220> FEATURE:
<223> OTHER INFORMATION: Rho 266 ribozyme cDNA

<400> SEQUENCE: 18
tcgacagagc gtctgatgag cggtcttcgg accgcgaaag gaagtctgca        50

<210> SEQ ID NO 19
<211> LENGTH: 42
<212> TYPE: DNA
<213> ORGANISM: artificial sequence
<220> FEATURE:
<223> OTHER INFORMATION: Rho 266 ribozyme

<400> SEQUENCE: 19
gtctcgcaga ctactcgcca gaagcctggc gctttccttc ag                42

<210> SEQ ID NO 20
<211> LENGTH: 36
<212> TYPE: DNA
<213> ORGANISM: artificial sequence
<220> FEATURE:
<223> OTHER INFORMATION: Rho cDNA primer

<400> SEQUENCE: 20
agtatggtac cagatctaag agtcatccag ctggag                       36

<210> SEQ ID NO 21
<211> LENGTH: 28
<212> TYPE: DNA
<213> ORGANISM: artificial sequence
<220> FEATURE:
<223> OTHER INFORMATION: Rho cDNA primer

<400> SEQUENCE: 21
gatcgtcgac ctactgtgtg ccccattc                                28
```

-continued

<210> SEQ ID NO 22
<211> LENGTH: 24
<212> TYPE: DNA
<213> ORGANISM: artificial sequence
<220> FEATURE:
<223> OTHER INFORMATION: PCR primer

<400> SEQUENCE: 22
aatttggagg gcttctttgc cacc                                          24

<210> SEQ ID NO 23
<211> LENGTH: 24
<212> TYPE: DNA
<213> ORGANISM: artificial sequence
<220> FEATURE:
<223> OTHER INFORMATION: rhodopsin PCR primer

<400> SEQUENCE: 23
agttgctcat gggcttacac acca                                          24

<210> SEQ ID NO 24
<211> LENGTH: 25
<212> TYPE: DNA
<213> ORGANISM: artificial sequence
<220> FEATURE:
<223> OTHER INFORMATION: PCR primer

<400> SEQUENCE: 24
aaattgccct gtggtccttg gtggt                                         25

<210> SEQ ID NO 25
<211> LENGTH: 24
<212> TYPE: DNA
<213> ORGANISM: artificial sequence
<220> FEATURE:
<223> OTHER INFORMATION: PCR primer

<400> SEQUENCE: 25
gactttgctt tccttggtca ggca                                          24

<210> SEQ ID NO 26
<211> LENGTH: 24
<212> TYPE: DNA
<213> ORGANISM: artificial sequence
<220> FEATURE:
<223> OTHER INFORMATION: PCR probe

<400> SEQUENCE: 26
ggcttatatc caacacttcg tggg                                          24

<210> SEQ ID NO 27
<211> LENGTH: 26
<212> TYPE: DNA
<213> ORGANISM: artificial sequence
<220> FEATURE:
<223> OTHER INFORMATION: PCR primer

<400> SEQUENCE: 27
tcaaggtcgc aagcttgctg gtgaaa                                        26

<210> SEQ ID NO 28
<211> LENGTH: 4172
<212> TYPE: RNA
<213> ORGANISM: artificial sequence
<220> FEATURE:
<223> OTHER INFORMATION: RPE65-IRES-SEAP

```
<400> SEQUENCE: 28
uccucauccu acagcuggua ccagaacucu cucuaaucuu cacuggaaga aaaugucuau    60
ccaaauugaa cacccugcug guggcuacaa gaaacuauuu gaaacugugg aggaacuguc   120
cucaccacua acagcucaug ucacaggcag gauucccuc uggcucacug gcagucuccu    180 ccgaugugg ccagggcucu uugaaguugg aucugagccu ucuaucacc uguuugaugg     240 acaagcccuu uugcacaagu uugacuucaa ggagggccau gucacauacc acagaagauu   300
cauccgcacu gaugcuuaug uucgagcaau gacugagaag aggauuguca uaacagaauu   360
uggcaccugu gcuuucccag accccugcaa gaauauauuu uccagguuuu uucuuacuu    420 uaaaggagua gagguuacug acaaugcccu uguaaauauc uacccagugg gagaagauua   480
cuaugcaugc acagagacca acuuuaucac aaagauuaac ccagagaccu uggagacaau   540
uaagcagguu gaucuuugca acuauauuuc ugucaauggu gccacugcuc auccacauau   600
ugaaagugau ggaacaguuu acaacauugg gaauugcuuu ggaaaaaauu uuacaguugc   660
cuacaacauu auuaagaucc cuccacugaa agcagacaag gaagauccaa uaaacaaguc   720
agaaguuguu gugcaguucc ccugcaguga ucguuucaag ccaucuuaug uacacaguuu   780
uggucugacu cccaacuaua ucguuuugu ggagacucca gucaaaauua accuuuucaa    840
guuucuuucu ucguggaguc uuggggagc aacuacaug gacuguuucg aguccaauga    900
aagcaugggg guuggcuuc auguugcuga uaaaaaaga agaaaauacu caauaacaa     960 auacaggacu uccccuuuca aucucuucca ucauaucaau acuuaugaag acaauggauu  1020
ucugauugug gaucucuguu gcuggaaagg guuugaauuu guuauaaauu acuuauauuu  1080
agccaauuua cgugagaauu gggaagaagu uaaaagaaau gcauagaagg cuccucagcc  1140
ugaagucagg agauaugua uuccuuugac aauugacaag gucgacacag gcagaaauuu   1200
agucacacug ccccauacaa cugccacagc cacucugcgc agugaugaga ccauauggcu   1260
ggaaccugag guucucuuuu cagggccucg ucaagccuuu gaauuccuc aaaucaauua   1320 ccagaaauuu ggagggaaac cuuauacuua ugcaucgga cuuggguuga ucacuuugu   1380 uccugacaag cucuguaaga ugaacgucaa aacuaaagaa aucuggaugu ggcaagagcc   1440
agauucuuac ccaucugaac ccaucuuugu uucucaacca gaugcucugg aagaaugaa   1500 uggugugguu cugagugugg uggugagccc uggggcaggg caaaagccug cauaucuccu   1560
gguucugaau gccaaagacu ugagugaaau ugccagggcu gaaguggaga cuaauauccc   1620
ugugaccuuc cauggacugu ucaaaagauc cugaacauau uccagagaug gcucagcagu   1680
acaacacuga cugcccuucu acagaucgug uguucaauuc ccaaagauca ccuggugacu   1740
cacuuccauc ugacggaa uccaaugccc ucuuaugcug uuucugaaga cagcaaaagu    1800
guacucauau auacauauga ucgacggguac cgcgggcccg ggauccgccc cucuccuccc   1860 ccccccua acguuacugg ccgaagccgc uuggaauaag gccggugugc guuugucuau    1920 auguuauuu ccaccauauu gccgucuuuu ggcaagugua gggcccggaa accuggcccu   1980
gucuucuuga cgagcauucc uaggggucuu uccccucucg ccaaaggaau gcaaggucug   2040
uugaaugucg ugaaggaagc aguuccucug gaagcuucuu gaagacaaac aacgucugua   2100
gcgacccuuu gcaggcagcg gaaccccca ccuggcgaca ggugccucug cggccaaaag    2160
ccacguguau aagauacacc ugcaaaggcg gcacaacccc agugccacgu ugugaguugg   2220
auaguugugg aaagagucaa auggcucucc ucaagcguau caacaagggg gcugaaggau   2280
gcccagaagg uaccccauug uaugggaucu gaucuggggc cucggugcac augcuuuaca   2340
```

```
uguguuuagu cgagguuaaa aaaacgucua ggccccccga accacgggga cgugguuuuc      2400
cuuugaaaaa cacgcaugaua auauggccac cgcccaccau gcugcugcug cugcugcugc      2460
ugggccugag gcuacagcuc ucccugggca ucaucccagu ugaggaggag aacccggacu      2520
ucuggaaccg cgaggcagcc gaggcccugg gugccgccaa gaagcugcag ccugcacaga      2580
cagccgccaa gaaccucauc aucuuccugg gcgauggau gggggugucu acggugacag       2640
cugccaggau ccuaaaaggg cagaagaagg acaaacuggg gccugagaua ccccuggcca      2700
uggaccgcuu cccauaugug gcucugucca agacauacaa uguagacaaa caugugccag      2760
acaguggagc cacagccacg gccuaccugu gcggggucaa gggcaacuuc cagaccauug      2820
gcuugagugc agccgcccgc uuuaaccagu gcaacacgac acgcggcaac gaggucaucu      2880
ccgugaugaa ucgggccaag aaagcaggga agucaguggg agugguaacc accacacgag      2940
ugcagcacgc cucgccagcc ggcaccuacg cccacacggu gaaccgcaac ugguacucgg      3000
acgccgacgu gccugcccg gcccgccagg aggggugcca ggacaucgcu acgcagcuca      3060
ucuccaacau ggacauugac gugauccuag guggaggccg aaaguacaug uuucgcaugg      3120
gaaccccaga cccugaguac ccagaugacu acagccaagg ugggaccagg cuggacggga      3180
agaaucuggu gcaggaaugg cuggcgaagc gccagggugc ccgguaugug uggaaccgca      3240
cugagcucau gcaggcuucc cuggacccgu cugugacccca ucaugggu cucuuugagc       3300 cuggagacau gaaauacgag auccaccgag acuccacacu ggaccccucc cugauggaga      3360
ugacagaggc ugcccugcgc cugcugagca ggaacccccg cggcuucuuc cucuucgugg      3420
aggguggucg caucgaccau ggucaucaug aaagcagggc uuaccgggca cugacugaga      3480
cgaucauguu cgacgacgcc auugagaggg cgggccagcu caccagcgag gaggacacgc      3540
ugagccucgu cacugccgac cacucccacg ucuucuccuu cggaggcuac ccccugcgag      3600
ggagcuccau cuucgggcug gccccuggca aggcccggga caggaaggcc uacacguucc      3660
uccuauacgg aaacggucca ggcuaugugc ucaaggacgg cgcccggccg gauguuaccg      3720
agagcgagag cgggagcccc gaguaucggc agcagucagc agugcccug gacgaagaga       3780 cccacgcagg cgaggacgug gcggguuucg cgcgcggccc gcaggcgcac cugguucacg      3840
gcgugcagga gcagaccuuc auagcgcacg ucauggccuu cgccgccugc cuggagcccu      3900
acaccgccug cgaccuggcg cccccgccg gcaccaccga cgccgcgcac ccggguuacu       3960
cuagagucga uaucggggcg gccggccgcu ucgagcagac augauaagau acauugauga      4020
guuuggacaa accacaacua gaaugcagug aaaaaaaugc uuuauuugug aaauuugug       4080 ugcuauugcu uucaauuguu guuguuaacu uguuuauugc agcuuauaau gguuacaaau      4140
aaagcaauag caucacaaau uucacaaaua aa                                    4172
```

<210> SEQ ID NO 29
<211> LENGTH: 3585
<212> TYPE: RNA
<213> ORGANISM: artificial sequence
<220> FEATURE:
<223> OTHER INFORMATION: RDH5-IRES-SEAP

<400> SEQUENCE: 29

```
acuccuggac cacagcgaga guccacccac uccagacuuu ggccuuagcu guagcuagug       60
ugggagccug ggaagucuag gagcaaaguc ucucaagcag acagaaagcu acagcuucac      120
acauugucuu gccugccagc uuccccagag ggcugcccuc agcagggcau cucaucccau      180
caugucgcug cccucugcuuc uggggccuu gcugugggca gugcuguggu ugcucagaga      240
```

| | |
|---|---|
| ccggcagagc cugccggcca gugaugcuuu caucuucauc acuggcugug acucuggcuu | 300 |
| ugggcgccuu cuggcacugc aacuugacca gaagggcuuc caaguccugg ccggcugccu | 360 |
| gaccccucu ggagcagaag accugcagca gauggccucc ucccgccucc acacaacacu | 420 |
| acuggauauc acugauccc agaaugucca gcaaguugcc aagugggug agacacgugu | 480 |
| uggagaaacu ggacuuuuug gucuggugaa uacgcuggc guagcuggua ucaucgggcc | 540 |
| cacaccaugg cuaacacagg augauuucca gagaguacug agugugaaca cacggggcc | 600 |
| caucggugu acccuugccc ugcugcccu gcuacagcag gccaggggc gggugcucaa | 660 |
| caucaccagu gucuugggcc gcauagcagc caauggcggg ggcuacugug ucuccaaguu | 720 |
| uggccuggag gccuucucug acagccugag gcgggacaug gcuccguucg gaguacaagu | 780 |
| cuccauugug gagccuggcu ucuuucgaac cccugugacc aaccuggaga gucuggagag | 840 |
| cacccugaag gcuuguuggg cccggcuacc uccagcuaua caggcccacu acggggaagc | 900 |
| cuuccucgau acuuaucuuc gaguacacg ccgcaucaug aaccgaucu gugacccaga | 960 |
| acuaacgaag gugaccagcu gccuggagca ugcccugacu gcucgccacc cccgaacacg | 1020 |
| cuacagccca ggcugggaug ccaagcgcuc cuggcugccu gccucuacc uccagccag | 1080 |
| gguggggau gcugugcuca ccuggauccu uccccggccc gccagucag ucuccugauu | 1140 |
| ccagcuuuac agcaagaggc ugauuuugaa aagcaaggca cuauuucug ugucuaccca | 1200 |
| gugcugccug guuucugaua ccaauuaggc ucuccgacgg uaccgcgggc ccgggauccg | 1260 |
| ccccucuccc ucccccccc cuaacguuac uggccgaagc cgcuuggaau aaggccggug | 1320 |
| ugcguuuguc uauauguuau uuccaccau auugccgucu uuuggcaaug ugagggcccg | 1380 |
| gaaaccuggc ccugucuucu ugacgagcau uccuaggggu cuuucccuc ucgccaaagg | 1440 |
| aaugcaaggu cuguugaaug ucgugaagga agcaguccu cuggaagcuu cuugaagaca | 1500 |
| aacaacgucu guagcgacc uuugcaggca gcggaacccc ccaccuggcg acaggugccu | 1560 |
| cugcggccaa aagccacgug uauaagauac accugcaaag gcggcacaac cccagugcca | 1620 |
| cguugugagu uggauaguug uggaaagagu caaauggcuc uccucaagcg uauucaacaa | 1680 |
| ggggcugaag gaugcccaga agguacccca uguauggga ucugaucugg ggccucggug | 1740 |
| cacaugcuuu acauguguuu agucgagguu aaaaaaacgu cuaggcccc cgaaccacgg | 1800 |
| ggacgugguu uccuuugaa aaacacgaug auaauauggc caccgcccac caugcugcug | 1860 |
| cugcugcugc ugcugggccu gaggcuacag cucucccugg gcaucauccc aguugaggag | 1920 |
| gagaacccgg acuucggaa ccgcgaggca gccgaggccc ugggcccgc caagaagcug | 1980 |
| cagccugcac agacagccgc caagaaccuc aucaucuucc ugggcgaugg gauggggug | 2040 |
| ucuacguga cagcugccag gauccuaaaa gggcagaaga aggacaaacu ggggccugag | 2100 |
| auaccccugg ccauggaccg cuucccauau guggcucugu ccaagacaua caaguagac | 2160 |
| aaacaugugc cagacagugg agccacagcc acggccuacc ugugcgggu caagggcaac | 2220 |
| uuccagacca uuggcuugag ugcagccgcc cgcuuuaacc agugcaacac gacacgcggc | 2280 |
| aacgagguca ucuccgugau gaacggggcc aagaaagcag ggaagucagu gggagugg ua | 2340 |
| accaccacac gagugcagca cgccucgcca gccggcaccu acgcccacac ggugaaccgc | 2400 |
| aacuggua cggacgccga cgugccugcc ucggcccgcc aggaggggug ccaggacauc | 2460 |
| gcuacgcagc ucaucuccaa cauggacauu gacgugaucc uaggugagg ccgaaaguac | 2520 |
| auguuucgca ugggaccccc agacccugag uaccagaug acuacagcca agguggggacc | 2580 |
| aggcuggacg ggaagaaucu ggugcaggaa uggcuggcga agcgccaggg ugcccggguau | 2640 |

```
gugugggaacc gcacugagcu caugcaggcu ucccuggacc cgucugugac ccaucucaug    2700
ggucucuuug agccuggaga caugaaauac gagauccacc gagacuccac acuggacccc    2760
ucccugaugg agaugacaga ggcugcccug cgccugcuga gcaggaaccc ccgcggcuuc    2820
uuccucuucg uggagggugg ucgcaucgac cauggucauc augaaagcag ggcuuaccgg    2880
gcacugacug agacgaucau guucgacgac gccauugaga gggcgggcca gcucaccagc    2940
gaggaggaca cgcugagccu cgucacugcc gaccacuccc acgucuucuc cuucggaggc    3000 uaccccugc gagggagcuc caucuucggg cuggccccug gcaaggcccg ggacaggaag    3060
gccuacacgg uccuccuaua cggaaacggu ccaggcuaug cucaagga cggcgcccgg     3120 ccggauguua ccgagagcga gagcgggagc cccgaguauc ggcagcaguc agcagugccc    3180
cuggacgaag agaccacgc aggcgaggac guggcggugu cgcgcgcgg cccgcaggcg     3240 caccugguuc acggcgugca ggagcagacc uucauagcgc acgucauggc cuucgccgcc    3300
ugccuggagc ccuacaccgc cugcgaccug gcgcccccg ccggcaccac cgacgccgcg    3360 cacccgggu acucuagagu cgauaucggg gcggccggcc gcuucgagca gacaugauaa    3420
gauacauuga ugaguuugga caaaccacaa cuagaaugca gugaaaaaaa ugcuuuauuu    3480
gugaaauuug ugaugcuauu gcuuucaauu guuguuguua acuuguuuau ugcagcuuau    3540
aaugguuaca aauaaagcaa uagcaucaca aauuucacaa auaaa                  3585
```

<210> SEQ ID NO 30
<211> LENGTH: 15
<212> TYPE: RNA
<213> ORGANISM: artificial sequence
<220> FEATURE:
<223> OTHER INFORMATION: GUU150 ribozyme containing NUH cleavage site

<400> SEQUENCE: 30
ucccaguuga ggagg                                                  15

<210> SEQ ID NO 31
<211> LENGTH: 15
<212> TYPE: RNA
<213> ORGANISM: artificial sequence
<220> FEATURE:
<223> OTHER INFORMATION: CUC246 ribozyme comprising NUH cleavage stie

<400> SEQUENCE: 31
agaaccucau caucu                                                  15

<210> SEQ ID NO 32
<211> LENGTH: 15
<212> TYPE: RNA
<213> ORGANISM: artificial sequence
<220> FEATURE:
<223> OTHER INFORMATION: CUA800 ribozyme comprising NUH cleavage site

<400> SEQUENCE: 32
gaugacuaca gccaa                                                  15

<210> SEQ ID NO 33
<211> LENGTH: 15
<212> TYPE: RNA
<213> ORGANISM: artificial sequence
<220> FEATURE:
<223> OTHER INFORMATION: AUA965 ribozyme  comprising NUH cleavage site

<400> SEQUENCE: 33
augaaauacg agauc                                                  15

```
<210> SEQ ID NO 34
<211> LENGTH: 15
<212> TYPE: RNA
<213> ORGANISM: artificial sequence
<220> FEATURE:
<223> OTHER INFORMATION: AUC1260 ribozyme comprising NUH cleavage site

<400> SEQUENCE: 34
gcuccaucuu cgggc                                                     15

<210> SEQ ID NO 35
<211> LENGTH: 15
<212> TYPE: RNA
<213> ORGANISM: artificial sequence
<220> FEATURE:
<223> OTHER INFORMATION: AUA1654 ribozyme comprising NUH cleavage site

<400> SEQUENCE: 35
auaagauaca uugau                                                     15

<210> SEQ ID NO 36
<211> LENGTH: 40
<212> TYPE: RNA
<213> ORGANISM: artificial sequence
<220> FEATURE:
<223> OTHER INFORMATION: SEAP 963 six base pair stem hhRz

<400> SEQUENCE: 36
gaucucgcug augagcgguc uucggaccgc gaaauuucau                          40

<210> SEQ ID NO 37
<211> LENGTH: 245
<212> TYPE: RNA
<213> ORGANISM: artificial sequence
<220> FEATURE:
<223> OTHER INFORMATION: ribozyme construct
<220> FEATURE:
<221> NAME/KEY: misc_feature
<222> LOCATION: (138)..(144)
<223> OTHER INFORMATION: n is a, c, g, or u
<220> FEATURE:
<221> NAME/KEY: misc_feature
<222> LOCATION: (172)..(177)
<223> OTHER INFORMATION: n is a, c, g, or u

<400> SEQUENCE: 37
gggcacucuu ccguggucug guggauaaau ucgcaagggu aucauggcgg acgaccgggg    60
uucgaacccc ggauccggcc guccgccgug auccaugcgg uuaccccgu guaaucaacc    120 acauacaaua agucgacnnn nnnncugaug agcggucuuc ggaccgcgaa annnnnncug   180
caguacuaca uauacaucca aacacggggg uaaccgacgu cagacaacgg gggagcgcuc   240
cuuuu                                                               245

<210> SEQ ID NO 38
<211> LENGTH: 81
<212> TYPE: RNA
<213> ORGANISM: artificial sequence
<220> FEATURE:
<223> OTHER INFORMATION: RHO 220-300

<400> SEQUENCE: 38
ccuacauguu ucugcugauc gugcugggcu uccccaucaa cuuccucacg cucuacguca   60 ccgucagca caagaagcug c                                              81
```

```
<210> SEQ ID NO 39
<211> LENGTH: 135
<212> TYPE: RNA
<213> ORGANISM: artificial sequence
<220> FEATURE:
<223> OTHER INFORMATION: RHO 698-832

<400> SEQUENCE: 39
gucuuuuguc aucuacaugu ucguggucca cuucaccauc cccaugauua ucaucuuuuu      60
cugcuauggg cagcucgucu ucaccgucaa ggaggccgcu gcccagcagc aggagucagc     120
caccacacag aaggc                                                      135
```